(12) United States Patent
Yamashita et al.

(10) Patent No.: US 9,878,981 B2
(45) Date of Patent: Jan. 30, 2018

(54) METHOD FOR PRODUCING HETEROCYCLIC COMPOUND
(71) Applicant: TAKEDA PHARMACEUTICAL COMPANY LIMITED, Osaka (JP)
(72) Inventors: Hironori Yamashita, Osaka (JP); Kazuhiro Miwa, Osaka (JP)
(73) Assignee: TAKEDA PHARMACEUTICAL COMPANY LIMITED, Osaka (JP)
( * ) Notice: Subject to any disclaimer, the term of this patent is extended or adjusted under 35 U.S.C. 154(b) by 0 days.
(21) Appl. No.: 15/301,525
(22) PCT Filed: Apr. 9, 2015
(86) PCT No.: PCT/JP2015/061075
§ 371 (c)(1),
(2) Date: Oct. 3, 2016
(87) PCT Pub. No.: WO2015/156346
PCT Pub. Date: Oct. 15, 2015

(65) Prior Publication Data
US 2017/0121286 A1    May 4, 2017

(30) Foreign Application Priority Data
Apr. 10, 2014   (JP) ................. 2014-080984

(51) Int. Cl.
 C07D 211/60        (2006.01)
 C07C 231/02        (2006.01)
 C07D 401/06        (2006.01)
(52) U.S. Cl.
 CPC .......... *C07D 211/60* (2013.01); *C07C 231/02* (2013.01); *C07D 401/06* (2013.01);
 (Continued)
(58) Field of Classification Search
 CPC ............................ C07D 211/60; C07C 231/02
 See application file for complete search history.

(56) References Cited

FOREIGN PATENT DOCUMENTS

| WO | 2007/077005 | 7/2007 |
| WO | 2009/154300 | 12/2009 |
| WO | 2013/095275 | 6/2013 |

OTHER PUBLICATIONS

International Search Report dated Jul. 7, 2015 in corresponding International Application No. PCT/JP2015/061075.
(Continued)

*Primary Examiner* — Golam M M Shameem
(74) *Attorney, Agent, or Firm* — Wenderoth, Lind & Ponack, L.L.P.

(57) ABSTRACT

Provided is a production method of a synthetic intermediate for a heterocyclic compound having a renin inhibitory activity and useful as a prophylactic or therapeutic drug for diabetic nephropathy, hypertension and the like. A production method of a compound represented by the formula (III-1a), the formula (III-1b), the formula (III-1c) and/or the formula (III-1d);

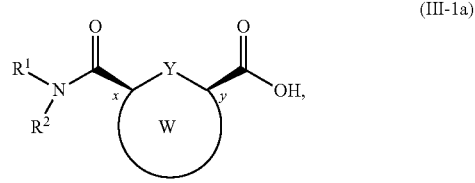

(III-1a)

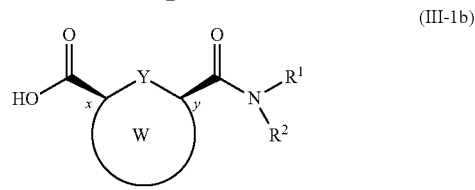

(III-1b)

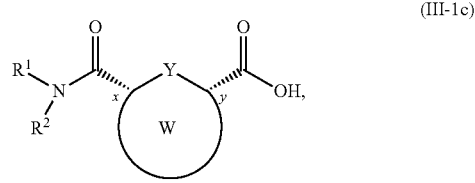

(III-1c)

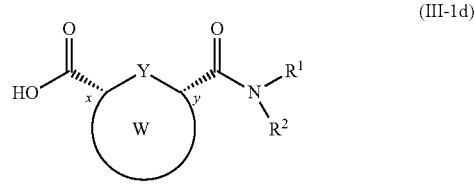

(III-1d)

wherein each symbol is as described in DESCRIPTION, or a salt thereof, including reacting a compound represented by the formula (Ia) or (Ib):

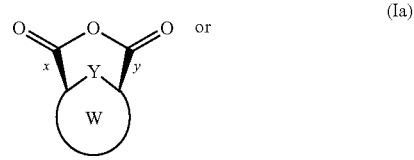

(Ia)

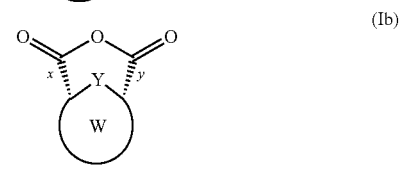

(Ib)

wherein each symbol is as described in DESCRIPTION, or a salt thereof with a compound represented by the formula (II):

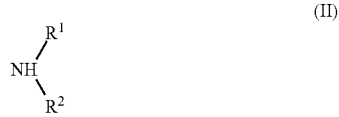

(II)

wherein each symbol is as described in DESCRIPTION, or a salt thereof, in the presence of an aluminum compound and a chiral amine compound.

12 Claims, No Drawings

(52) U.S. Cl.
CPC ...... *C07C 2101/02* (2013.01); *C07C 2101/08* (2013.01); *C07C 2101/16* (2013.01)

(56) References Cited

OTHER PUBLICATIONS

Tanyeli et al., "Asymmetric synthesis of 1,4-amino alcohol ligands with a norbornene backbone for use in the asymmetric diethylzinc addition to benzaldehyde", Tetrahedron: *Asymmetry*, 16(11), pp. 2039-2043, 2005.

First Office Action dated Sep. 11, 2017 in Chinese Application No. 201580031067.4, with English translation.

Wagh et al., "Reactions of Cyclic Anhydrides: Part VI. Transesterification of Maleanilic & Fumaranilic Acids with Phosphorus Pentoxide-Alkanol", Indian Journal of Chemistry, Section B: Organic Chemistry Including Medicinal Chemistry, vol. 21B, No. 6, 1982, pp. 577-578.

METHOD FOR PRODUCING HETEROCYCLIC COMPOUND

TECHNICAL FIELD

The present invention relates to a production method of a heterocyclic compound.

BACKGROUND OF THE INVENTION

A heterocyclic compound represented by the following formula having a superior renin inhibitory activity and useful as a prophylactic or therapeutic drug for diabetic nephropathy, hypertension and the like is disclosed in patent document 1.

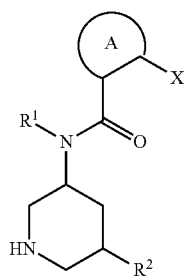
(I)

wherein each symbol is as described in patent document 1.

Patent document 1 discloses the following method as a production method of a synthetic intermediate for the above-mentioned heterocyclic compound.

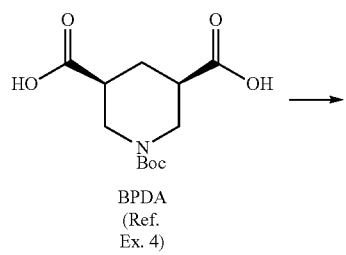
BPDA
(Ref. Ex. 4)

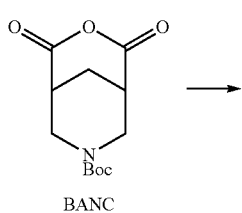
BANC

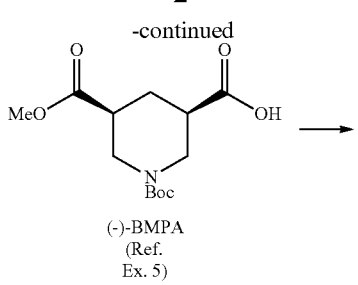
(−)-BMPA
(Ref. Ex. 5)

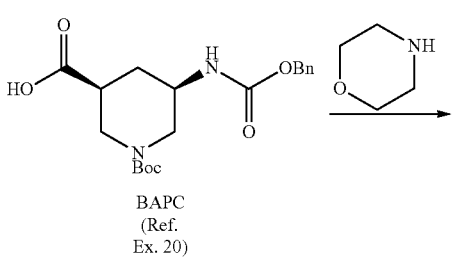
BAPC
(Ref. Ex. 20)

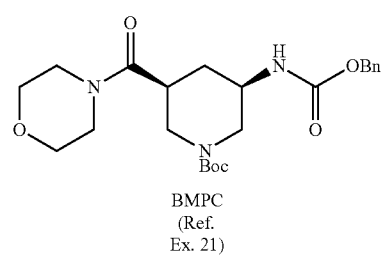
BMPC
(Ref. Ex. 21)

In the above-mentioned method, chiral dicarboxylic acid monoester ((−)-BMPA) is synthesized from acid anhydride (BANC), and then carboxylic acid (BAPC) is obtained via conversion to Z-protected amine by Curtius rearrangement of carboxylic acid and hydrolysis, and amidation by a condensation reaction with amine (morpholine) is performed to synthesize a heterocyclic amide compound (BMPC).

In addition, patent document 2 discloses a production method of a compound useful as a synthetic intermediate for the above-mentioned heterocyclic compound.

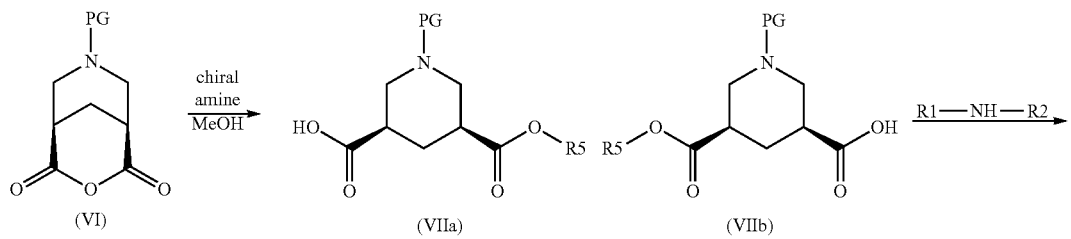

-continued

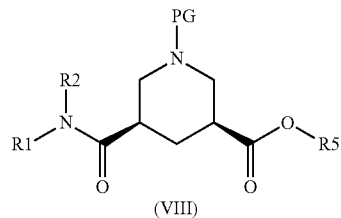

(VIII)

wherein each symbol is as described in patent document 2.

In the above-mentioned method, a chiral dicarboxylic acid monoester compound represented by the formula (VIIa) or (VIIb) is produced from acid anhydride represented by the formula (VI) in the presence of chiral amine, which is then reacted with amine (R1-NH—R2) to perform amidation, whereby a heterocyclic amide compound represented by the formula (VIII) is produced.

DOCUMENT LIST

Patent Documents patent document 1: JP-B-4800445
patent document 2: WO 2007/077005

SUMMARY OF THE INVENTION

Problems to be Solved by the Invention

A convenient method of enantioselectively or diastereoselectively amidating an acid anhydride has been desired. That is, the present invention aims to provide a method of enantioselectively or diastereoselectively amidating an acid anhydride.

Means of Solving the Problems

The present inventors have conducted various intensive studies and found a method of amidating an acid anhydride, which is convenient and having high enantioselectivity or diastereoselectivity, which resulted in the completion of the present invention.

That is, the present invention relates to
[1] a production method of a compound represented by the formula (III-1a), the formula (III-1b), the formula (III-1c) and/or the formula (III-1d);

(III-1a)

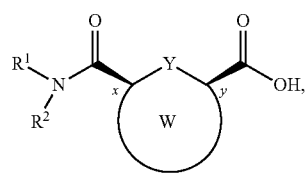

(III-1b)

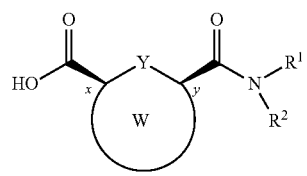

(III-1c)

(III-1d)

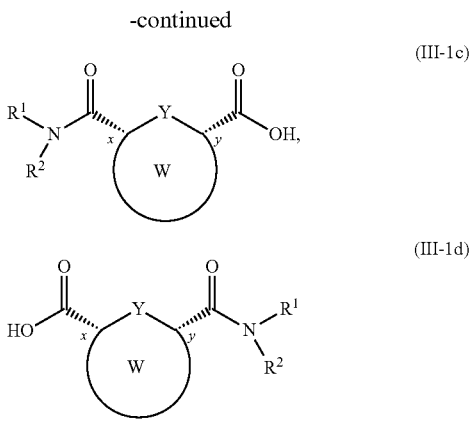

wherein $R^1$ and $R^2$ are each independently a hydrogen atom or a substituent, or $R^1$ and $R^2$ are optionally bonded to each other to form an optionally substituted ring;

ring W is an optionally substituted ring;

Y is a carbon atom or a bond; and x and y are each a bond, or a salt thereof, comprising reacting a compound represented by the formula (Ia) or (Ib):

(Ia)

(Ib)

wherein each symbol is as defined above, or a salt thereof, with a compound represented by the formula (II):

(II)

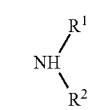

wherein each symbol is as defined above, or a salt thereof, in the presence of an aluminum compound and a chiral amine compound;

[2] the production method of the aforementioned [1], wherein the ring W is a ring represented by the formula:

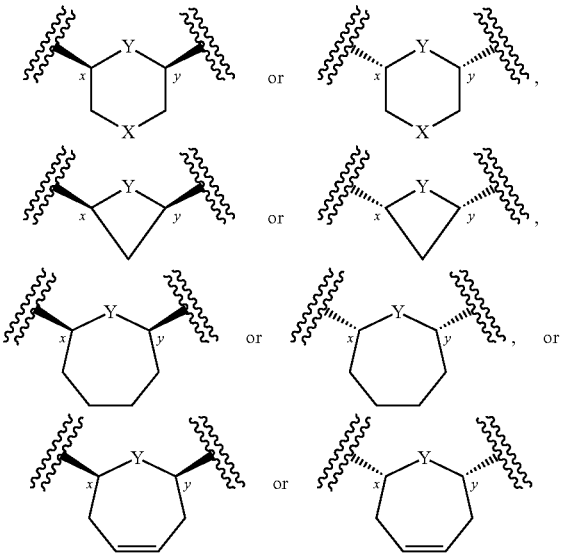

wherein
X is an optionally substituted carbon atom or an optionally substituted nitrogen atom,
and other symbols are as defined above;
[3] the production method of the aforementioned [1], wherein the ring W is a ring represented by the formula:

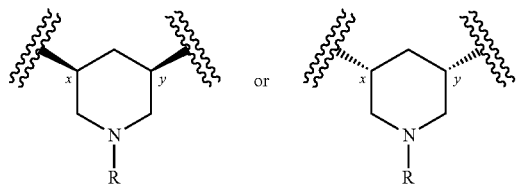

wherein
R is an amino-protecting group,
and other symbols are as defined above;
[4] the production method of the aforementioned [3], wherein R is a tertiary-butoxycarbonyl group;
[5] the production method of any one of the aforementioned [1]-[4], wherein the chiral amine compound is cinchona alkaloid;
[6] the production method of the aforementioned [5], wherein cinchona alkaloid is quinine;
[7] the production method of any one of the aforementioned [1]-[6], wherein $R^1$ and $R^2$ in the compound represented by the formula (II) are each independently a hydrogen atom, an optionally substituted $C_{1-6}$ alkyl group or an optionally substituted $C_{1-6}$ alkoxy group; or $R^1$ and $R^2$ are bonded to each other to form a non-aromatic heterocycle;
[8] the production method of any one of the aforementioned [1]-[6], wherein the compound represented by the formula (II) is morpholine or a salt thereof;
[9] the production method of any one of the aforementioned [1]-[8], wherein the aluminum compound is dialkylaluminum hydride, dihalogenated aluminum hydride, monohalogenated monoalkylaluminum hydride, trialkylaluminum, trihalogenated aluminum, monohalogenated dialkylaluminum or dihalogenated monoalkylaluminum;
[10] the production method of any one of the aforementioned [1]-[8], wherein the aluminum compound is diisobutylaluminum hydride;
[11] a production method of (3S,5R)-1-(tertiary-butoxycarbonyl)-5-(morpholin-4-ylcarbonyl)piperidine-3-carboxylic acid or a salt thereof, comprising reacting tertiary-butyl 2,4-dioxo-3-oxa-7-azabicyclo[3.3.1]nonane-7-carboxylate or a salt thereof with morpholine in the presence of an aluminum compound and a chiral amine compound;
[12] a production method of 1-(4-methoxybutyl)-N-(2-methylpropyl)-N-[(3S,5R)-5-(morpholin-4-ylcarbonyl)piperidin-3-yl]-1H-benzimidazole-2-carboxamide or a salt thereof, comprising a step of producing (3S,5R)-1-(tertiary-butoxycarbonyl)-5-(morpholin-4-ylcarbonyl)piperidine-3-carboxylic acid or a salt thereof by reacting tertiary-butyl 2,4-dioxo-3-oxa-7-azabicyclo[3.3.1]nonane-7-carboxylate or a salt thereof with morpholine in the presence of an aluminum compound and a chiral amine compound;
and the like.

Effect of the Invention

By the production method of the present invention, acid anhydride can be amidated in one step with high enantioselectivity or diastereoselectivity, and therefore, the production step can be shortened and the production cost can be reduced.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),

(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered nonaromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclyl-sulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl)($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents of the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a nonaromatic heterocyclic group and (iii) a 7- to 10-membered crosslinked heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzoisoxazolyl, benzothiazolyl, benzoisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "nonaromatic heterocyclic group" (including "3- to 14-membered nonaromatic heterocyclic group") include a 3- to 14-membered (preferably 4- to 10-membered) nonaromatic heterocyclic group containing, as a ring-constituting atom besides carbon atom, 1 to 4 hetero atoms selected from a nitrogen atom, a sulfur atom and an oxygen atom.

Preferable examples of the "nonaromatic heterocyclic group" include 3- to 8-membered monocyclic nonaromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) nonaromatic heterocyclic groups such as dihydrobenzofuranyl, dihydrobenzoimidazolyl, dihydrobenzoxazolyl, dihydrobenzothiazolyl, dihydrobenzoisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzoazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered crosslinked heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constitution atom.

In the present specification, examples of the "optionally substituted heterocyclic group" include a heterocyclic group optionally having substituent(s) selected from the aforementioned substituent group A.

The number of the substituents of the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered nonaromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclyl-sulfonyl group, a hydrocarbon-sulfinyl group and a heterocyclyl-sulfinyl group.

Here, the hydrocarbon-sulfonyl group means a hydrocarbon group-bonded sulfonyl group, the heterocyclyl-sulfonyl group means a heterocyclic group-bonded sulfonyl group, the hydrocarbon-sulfinyl group means a hydrocarbon group-bonded sulfinyl group and the heterocyclyl-sulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{5-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-5}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-5}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-5}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-5}$ alkyl-carbamoyl)amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl)($C_{1-6}$ alkyl-carbonyl)amino group (e.g., N-acetyl-N-methylamino) and a ($C_{1-6}$ alkyl)($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, triazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and a 8- to 14-membered fused polycyclic (preferably bi or tricyclic) aromatic heterocycle such as benzothiophene, benzofuran, benzimidazole, benzoxazole, benzoisoxazole, benzothiazole, benzoisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiine, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxathiine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include a 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane and the like; and 9- to 14-membered fused polycyclic (preferably di or tricyclic) non-aromatic heterocycles such as dihydrobenzofuran, dihydrobenzoimidazole, dihydrobenzooxazole, dihydrobenzothiazole, dihydrobenzoisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzoazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

In the present specification, the "ring" of the "optionally substituted ring" includes the above-mentioned "hydrocarbon ring" and "heterocycle", and the substituent thereof includes the above-mentioned "substituent".

The production method of the present invention is described in detail below.

The production method of the present invention is a method of producing a compound represented by the formula (III-1a), the formula (III-1b), the formula (III-1c) and/or the formula (III-1d);

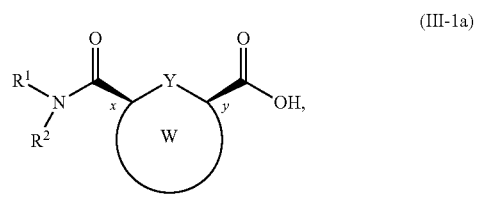

(III-1a)

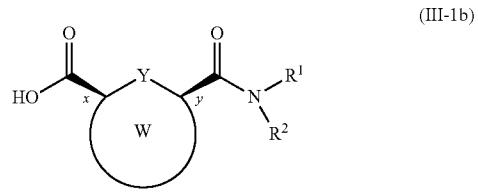

(III-1b)

-continued

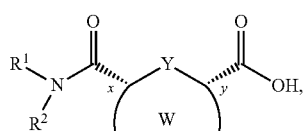
(III-1c)

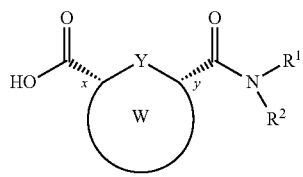
(III-1d)

wherein each symbol is as defined above, or a salt thereof, comprising reacting a compound represented by the formula (Ia) or (Ib):

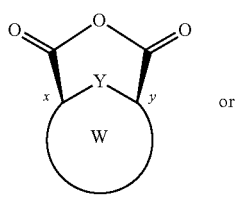
(Ia)

or

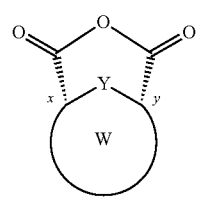
(Ib)

wherein each symbol is as defined above, or a salt thereof, with a compound represented by the formula (II):

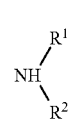
(II)

wherein each symbol is as defined above, or a salt thereof, in the presence of an aluminum compound and a chiral amine compound.

That is, the production method of the present invention is a method of producing an amide compound represented by the formula (III-1a), the formula (III-1b), the formula (III-1c) and/or the formula (III-1d) by amidating an acid anhydride represented by the formula (Ia) or (Ib) enantioselectively or diastereoselectively by using an amine represented by the formula (II) in the presence of an aluminum compound and a chiral amine compound.

The "ring" of the "optionally substituted ring" for ring W is preferably a ring represented by the formula:

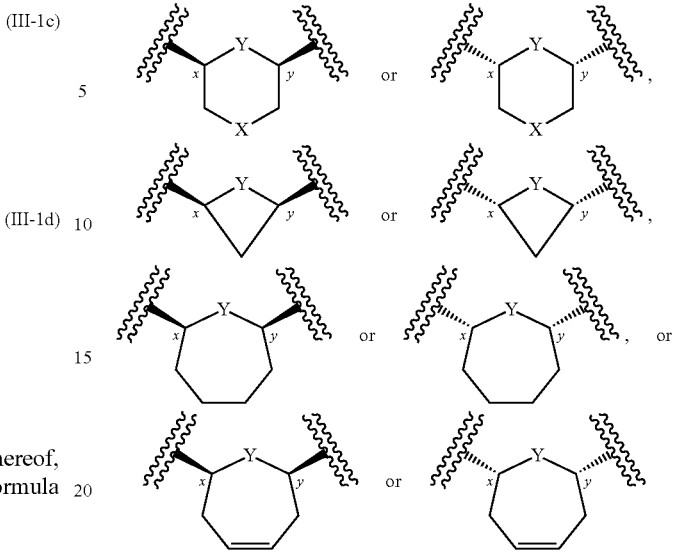

wherein each symbol is as defined above (e.g., piperidine ring, cyclopropane ring, cyclopentane ring, cyclohexane ring, a cyclohexene ring), more preferably a ring represented by the formula:

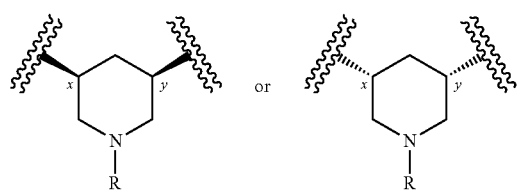

wherein each symbol is as defined above (i.e., piperidine ring).

The "ring" of the "optionally substituted ring" for ring W is optionally further substituted by 1 to 3 substituents at substitutable position(s). As such "substituent", an optionally substituted $C_{1-6}$ alkyl group (e.g., methyl), an optionally substituted $C_{1-6}$ alkyl-carbonyl group (e.g., acetyl), an optionally substituted $C_{1-6}$ alkoxy-carbonyl group (e.g., tertiary-butoxycarbonyl), or an optionally substituted $C_{6-14}$ arylsulfonyl group (e.g., phenylsulfonyl) is preferable, and a $C_{1-6}$ alkyl group (e.g., methyl) optionally substituted by 1 to 3 $C_{6-14}$ aryl groups (e.g., phenyl), a $C_{1-6}$ alkyl-carbonyl group (e.g., acetyl) optionally substituted by 1 to 3 halogen atoms (e.g., fluorine atom), a $C_{1-6}$ alkoxy-carbonyl group (e.g., tertiary-butoxycarbonyl) or a $C_{6-14}$ arylsulfonyl group (e.g., phenylsulfonyl) optionally substituted by nitro is more preferable. When plural substituents are present, the substituents may be the same or different.

The "substituent" of the "optionally substituted carbon atom" or "optionally substituted nitrogen atom" for X and the "amino-protecting group" for R are included in the "substituent" of the "optionally further substituted ring" for ring W explained above.

As the "amino-protecting group" for R, a $C_{1-6}$ alkyl group (e.g., methyl) optionally substituted by 1 to 3 $C_{6-14}$ aryl groups (e.g., phenyl), a $C_{1-6}$ alkyl-carbonyl group (e.g., acetyl) optionally substituted by 1 to 3 halogen atoms (e.g., fluorine atom), a $C_{1-6}$ alkoxy-carbonyl group (e.g., tertiary-butoxycarbonyl) or a $C_{6-14}$ arylsulfonyl group (e.g., phenylsulfonyl) optionally substituted by nitro is preferable, a $C_{1-6}$ alkoxy-carbonyl group (e.g., tertiary-butoxycarbonyl) is more preferable, and tertiary-butoxycarbonyl is particularly preferable.

As the "substituent" for $R^1$ or $R^2$, an optionally substituted $C_{1-6}$ alkyl group (e.g., methyl, ethyl, butyl) or an optionally substituted $C_{1-6}$ alkoxy group (e.g., methoxy) is preferable, a $C_{1-6}$ alkyl group (e.g., methyl, ethyl, butyl) optionally substituted by $C_{1-6}$ alkoxy group (e.g., methoxy) or a $C_{1-6}$ alkoxy group (e.g., methoxy) is more preferable.

As the "ring" of the "optionally substituted ring" formed by $R^1$ and $R^2$ bonded to each other, a non-aromatic heterocycle (e.g., pyrrolidine ring, piperidine ring, morpholine ring, thiomorpholine ring) is preferable, and a pyrrolidine ring, a piperidine ring, a morpholine ring or a thiomorpholine ring is more preferable.

The "optionally substituted ring" formed by $R^1$ and $R^2$ bonded to each other is optionally further substituted by 1 to 3 substituents at substitutable position(s). As such "substituent", the above-mentioned "substituent" can be mentioned. When plural substituents are present, the substituents may be the same or different.

$R^1$ and $R^2$ are each preferably independently a hydrogen atom, an optionally substituted $C_{1-6}$ alkyl group (e.g., methyl, ethyl, butyl) or an optionally substituted $C_{1-6}$ alkoxy group (e.g., methoxy), more preferably, a hydrogen atom, a $C_{1-6}$ alkyl group (e.g., methyl, ethyl, butyl) optionally substituted by a $C_{1-6}$ alkoxy group (e.g., methoxy) or a $C_{1-6}$ alkoxy group (e.g., methoxy). In another embodiment, $R^1$ and $R^2$ are preferably bonded to each other to form a non-aromatic heterocycle (e.g., pyrrolidine ring, piperidine ring, a morpholine ring, thiomorpholine ring), more preferably a pyrrolidine ring, a piperidine ring, a morpholine ring or a thiomorpholine ring, particularly preferably a morpholine ring.

Preferable examples of ring W, $R^1$, $R^2$, substituent and the like explained above are more preferably used in combination.

Preferable examples of the compound represented by the formula (III-1a), the formula (III-1b), the formula (III-1c) and/or the formula (III-1d) include the following compounds.

(A) A compound represented by the formula (III-1a), the formula (III-1b), the formula (III-1c) and/or the formula (III-1d), wherein ring W is a ring represented by the formula:

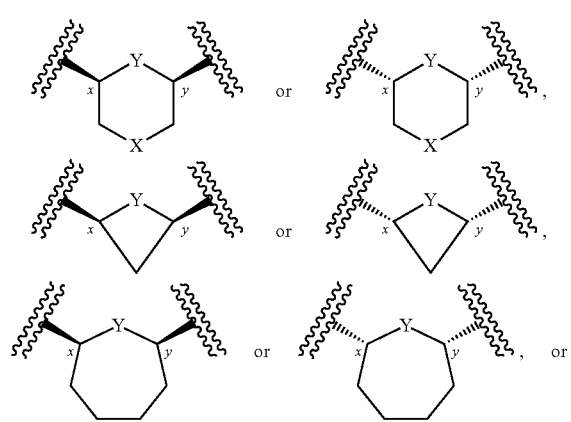

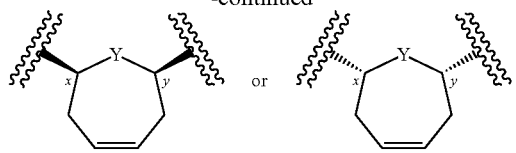

wherein each symbol is as defined above (e.g., piperidine ring, cyclopropane ring, cyclopentane ring, cyclohexane ring, a cyclohexene ring) (more preferably, ring represented by the formula:

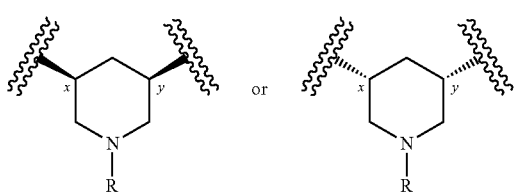

wherein each symbol is as defined above (i.e., piperidine ring)), each of which is optionally further substituted by 1 to 3 substituents selected from an optionally substituted $C_{1-6}$ alkyl group (e.g., methyl), an optionally substituted $C_{1-6}$ alkyl-carbonyl group (e.g., acetyl), an optionally substituted $C_{1-6}$ alkoxy-carbonyl group (e.g., tertiary-butoxycarbonyl) and an optionally substituted $C_{6-14}$ arylsulfonyl group (e.g., phenylsulfonyl); and $R^1$ and $R^2$ are each independently a hydrogen atom, an optionally substituted $C_{1-6}$ alkyl group (e.g., methyl, ethyl, butyl) or an optionally substituted $C_{1-6}$ alkoxy group (e.g., methoxy).

(B) A compound represented by the formula (III-1a), the formula (III-1b), the formula (III-1c) and/or the formula (III-1d), wherein ring W is a ring represented by the formula:

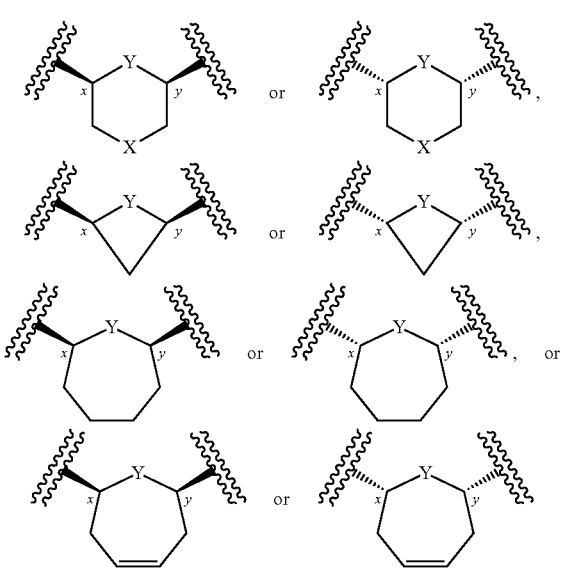

wherein each symbol is as defined above (e.g., piperidine ring, cyclopropane ring, cyclopentane ring, cyclohexane ring, a cyclohexene ring) (more preferably, ring represented by the formula:

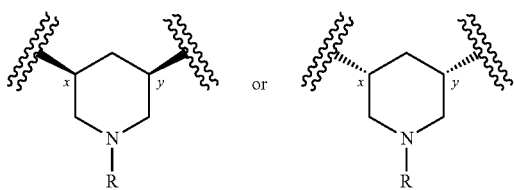

wherein each symbol is as defined above (i.e., piperidine ring)), each of which is optionally further substituted by 1 to 3 substituents selected from a $C_{1-6}$ alkyl group (e.g., methyl) optionally substituted by 1 to 3 $C_{6-14}$ aryl groups (e.g., phenyl), a $C_{1-6}$ alkyl-carbonyl group (e.g., acetyl) optionally substituted by 1 to 3 halogen atoms (e.g., fluorine atom), a $C_{1-6}$ alkoxy-carbonyl group (e.g., tertiary-butoxycarbonyl) and a $C_{6-14}$ arylsulfonyl group (e.g., phenylsulfonyl) optionally substituted by nitro; and $R^1$ and $R^2$ are each independently a hydrogen atom, a $C_{1-6}$ alkyl group (e.g., methyl, ethyl, butyl) optionally substituted by $C_{1-6}$ alkoxy group (e.g., methoxy) or a $C_{1-6}$ alkoxy group (e.g., methoxy).

(C) A compound represented by the formula (III-1a), the formula (III-1b), the formula (III-1c) and/or the formula (III-1d), wherein ring W is a ring represented by the formula:

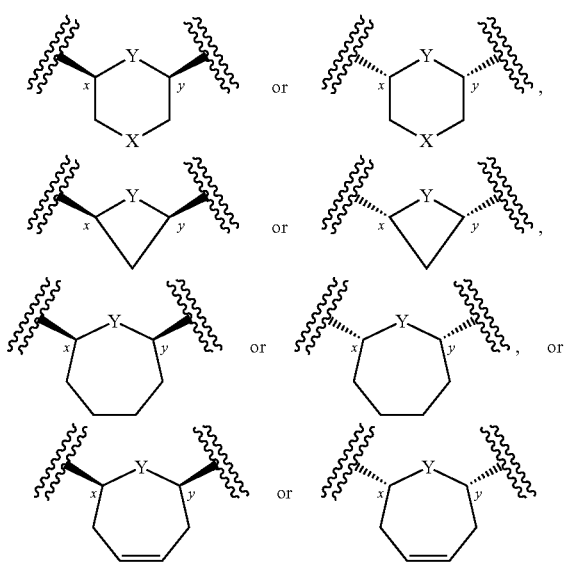

wherein each symbol is as defined above (e.g., piperidine ring, cyclopropane ring, cyclopentane ring, cyclohexane ring, a cyclohexene ring) (more preferably, ring represented by the formula:

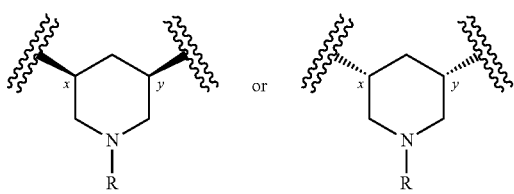

wherein each symbol is as defined above (i.e., piperidine ring)), each of which is optionally further substituted by 1 to 3 substituents selected from an optionally substituted $C_{1-6}$ alkyl group (e.g., methyl), an optionally substituted $C_{1-6}$ alkyl-carbonyl group (e.g., acetyl), an optionally substituted $C_{1-6}$ alkoxy-carbonyl group (e.g., tertiary-butoxycarbonyl) and an optionally substituted $C_{6-14}$ arylsulfonyl group (e.g., phenylsulfonyl); and $R^1$ and $R^2$ are bonded to each other to form non-aromatic heterocycle (e.g., pyrrolidine ring, piperidine ring, morpholine ring, thiomorpholine ring).

(D) A compound represented by the formula (III-1a), the formula (III-1b), the formula (III-1c) and/or the formula (III-1d), wherein ring W is a ring represented by the formula:

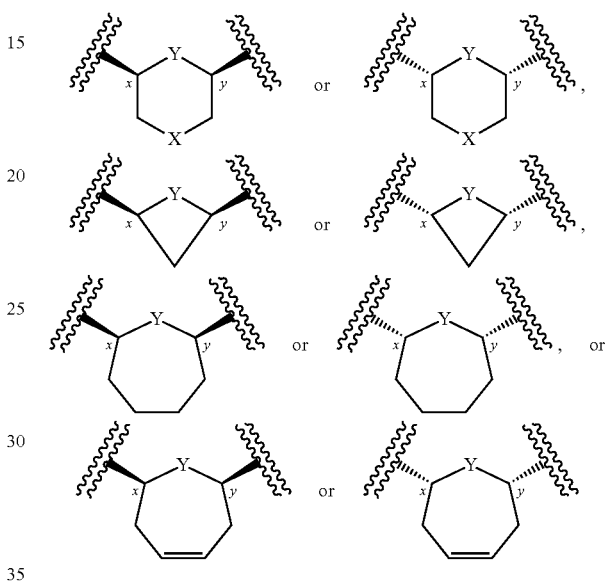

wherein each symbol is as defined above (e.g., piperidine ring, cyclopropane ring, cyclopentane ring, cyclohexane ring, a cyclohexene ring) (more preferably, ring represented by the formula:

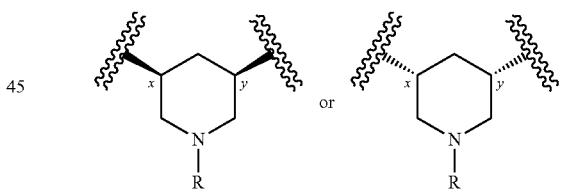

wherein each symbol is as defined above (i.e., piperidine ring)), each of which is optionally further substituted by 1 to 3 substituents selected from a $C_{1-6}$ alkyl group (e.g., methyl) optionally substituted by 1 to 3 $C_{6-14}$ aryl groups (e.g., phenyl), a $C_{1-6}$ alkyl-carbonyl group (e.g., acetyl) optionally substituted by 1 to 3 halogen atoms (e.g., fluorine atom), a $C_{1-6}$ alkoxy-carbonyl group (e.g., tertiary-butoxycarbonyl) and a $C_{6-14}$ arylsulfonyl group (e.g., phenylsulfonyl) optionally substituted by nitro; and $R^1$ and $R^2$ are bonded to each other to form a pyrrolidine ring, a piperidine ring, a morpholine ring, or a thiomorpholine ring.

The amount of a compound represented by the formula (II) (amine) or a salt thereof to be used is generally 1.0-2.0 mol, preferably 1.0-1.1 mol, per 1 mol of a compound represented by the formula (Ia) or (Ib) (acid anhydride) or a salt thereof.

In a preferable embodiment of the present invention, a compound represented by the formula (II) (amine) is morpholine.

Examples of the "aluminum compound" to be used in the production method of the present invention include alkylaluminum such as trimethylaluminum, triethylaluminum, triisobutylaluminum and the like; aluminum halide such as aluminum trichloride, aluminum tribromide and the like; alkylaluminum halide such as ethylaluminum dichloride, diethylaluminum chloride and the like; diisobutylaluminum hydride (DIBAL) and the like. From the aspect of selectivity, alkylaluminum or DIBAL is preferable and, from the aspect of handling safety, DIBAL is more preferable.

In another embodiment of the present invention, an aluminum compound is preferably dialkylaluminum hydride (e.g., diisobutylaluminum hydride), dihalogenated aluminum hydride (e.g., dichloroaluminum hydride), monohalogenated monoalkylaluminum hydride (e.g., chloro(methyl) aluminum hydride), trialkylaluminum (e.g., trimethylaluminum, triethylaluminum, triisobutylaluminum), trihalogenated aluminum (e.g., aluminum trichloride, aluminum tribromide), monohalogenated dialkylaluminum (e.g., diethylaluminum chloride) or dihalogenated monoalkylaluminum (e.g., ethylaluminum dichloride), more preferably dialkylaluminum hydride (e.g., diisobutylaluminum hydride), particularly preferably diisobutylaluminum hydride.

The amount of the aluminum compound to be used is generally 1.0-2.0 mol, preferably 1.0-1.1 mol, per 1 mol of a compound represented by the formula (Ia) or (Ib) (acid anhydride) or a salt thereof. When the amount of the aluminum compound to be used is less than 1.0 mol, a sufficient chiral reaction field is difficult to construct, thus resulting in degraded selectivity. By setting the amount of the aluminum compound to be used to not less than 1.0 mol, more chiral reaction fields are formed and the selectivity is improved.

Examples of the "chiral amine compound" to be used in the production method of the present invention include cinchona alkaloid such as quinine, quinidine, hydroquinine, hydroquinidine, cinchonine, cinchonidine and the like. From the aspect of selectivity, quinine, quinidine, hydroquinine or hydroquinidine is preferable, and quinine is more preferable.

The amount of the chiral amine compound to be used is generally 1.0-2.0 mol, preferably 1.0-1.1 mol, per 1 mol of a compound represented by the formula (Ia) or (Ib) (acid anhydride) or a salt thereof.

The amidation in the production method of the present invention can be performed generally in a solvent inert to the reaction. Examples of the solvent include aromatic hydrocarbons such as benzene, toluene, xylene and the like; ethers such as tetrahydrofuran (THF), dimethoxyethane, dioxane, diethyl ether and the like; amides such as N,N-dimethylformamide (DMF), dimethylacetamide (DMA) and the like; alcohols such as methanol, ethanol, propanol, tert-butanol, methoxyethanol and the like; sulfoxides such as dimethyl sulfoxide (DMSO) and the like; water; and a mixed solvent thereof.

The amidation in the production method of the present invention may be performed in the presence of a base in an attempt to improve nucleophilicity of a compound represented by the formula (II) (amine), and facilitate construction of a chiral reaction field. Examples of the base include basic salts such as sodium carbonate, potassium carbonate, cesium carbonate, sodium hydrogen carbonate and the like; organic bases such as 1,8-diazabicyclo[5.4.0]-7-undecene (DBU) and the like; metal alkoxides such as sodium tert-butoxide, potassium tert-butoxide and the like; alkali metal hydrides such as sodium hydride and the like; metal amides such as hexamethyldisilazane lithium and the like; organic lithiums such as normal butyllithium and the like; and Grignard reagents such as isopropylmagnesium chloride and the like.

The amount of the base to be used is generally 0.9-1.1 mol, per 1 mol of a compound represented by the formula (Ia) or (Ib) (acid anhydride) or a salt thereof.

Examples of the salt of a compound represented by the formula (Ia) or (Ib) (acid anhydride) include inorganic salts such as alkali metal salt (e.g., sodium salt, potassium salt etc.), alkaline earth metal salt (e.g., calcium salt, magnesium salt etc.) and the like, ammonium salt, and the like when an acidic functional group is contained in the compound, and salts with inorganic acids such as hydrochloric acid, hydrobromic acid, nitric acid, sulfuric acid, phosphoric acid and the like, and salts with organic acids such as acetic acid, phthalic acid, fumaric acid, oxalic acid, tartaric acid, maleic acid, citric acid, succinic acid, methanesulfonic acid, benzenesulfonic acid, p-toluenesulfonic acid and the like when a basic functional group is contained in the compound.

Examples of the salt of a compound represented by the formula (II) (amine) include salts with inorganic acids such as hydrochloric acid, hydrobromic acid, nitric acid, sulfuric acid, phosphoric acid and the like, salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

A compound represented by the formula (Ia) or (Ib) (acid anhydride) and a compound represented by the formula (II) (amine) or a salt thereof to be used may be commercially available products, or can also be produced by a method known per se or a method analogous thereto.

While the reaction time of the amidation in the production method of the present invention may vary depending on the reagents and solvents to be used and temperature, it is generally 10 min-4 hr, preferably 2-4 hr. While the reaction temperature may vary depending on the reagents and solvents to be used, it is generally −78° C. to 25° C., preferably −50° C. to −40° C.

Preferable examples of the production method of the present invention include the following.

(Production Method A1)

A production method of a compound represented by the formula (III-1a), the formula (III-1b), the formula (III-1c) and/or the formula (III-1d) or a salt thereof, comprising reacting a compound represented by the formula (Ia) or (Ib) or a salt thereof, wherein ring W is a ring represented by the formula:

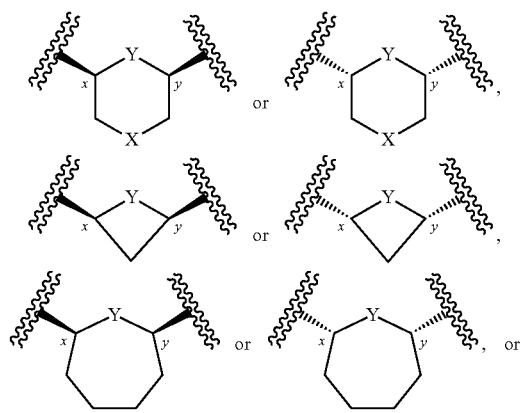

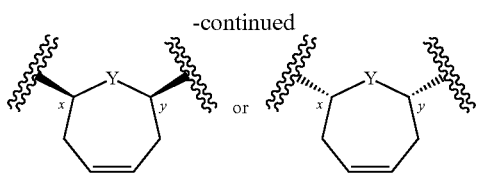 or

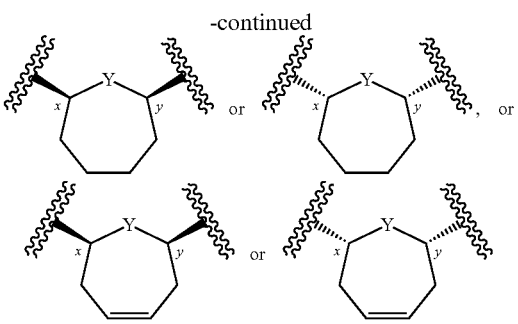, or

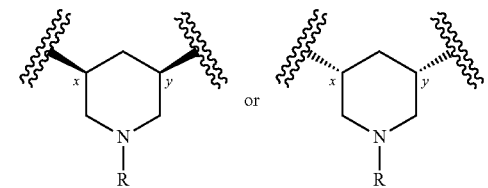

wherein each symbol is as defined above (e.g., piperidine ring, cyclopropane ring, cyclopentane ring, cyclohexane ring, a cyclohexene ring), each of which is optionally further substituted by 1 to 3 substituents selected from an optionally substituted $C_{1-6}$ alkyl group (e.g., methyl), an optionally substituted $C_{1-6}$ alkyl-carbonyl group (e.g., acetyl), an optionally substituted $C_{1-6}$ alkoxy-carbonyl group (e.g., tertiary-butoxycarbonyl) and an optionally substituted $C_{6-14}$ arylsulfonyl group (e.g., phenylsulfonyl), with a compound represented by the formula (II) or a salt thereof wherein $R^1$ and $R^2$ of the formula (II) are each independently a hydrogen atom, an optionally substituted $C_{1-6}$ alkyl group (e.g., methyl, ethyl, butyl) or an optionally substituted $C_{1-6}$ alkoxy group (e.g., methoxy), in the presence of an aluminum compound selected from alkylaluminum and DIBAL, and cinchona alkaloid (e.g., quinine, quinidine, hydroquinine, hydroquinidine, cinchonine, cinchonidine).

(Production Method A2)

A production method of a compound represented by the formula (III-1a), the formula (III-1b), the formula (III-1c) and/or the formula (III-1d) or a salt thereof, wherein, in the aforementioned production method A1, ring W is a ring represented by the formula:

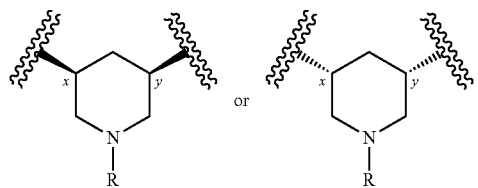

wherein each symbol is as defined above (i.e., piperidine ring), the aluminum compound is DIBAL, and cinchona alkaloid is selected from quinine, quinidine, hydroquinine and hydroquinidine.

(Production Method B1)

A production method of a compound represented by the formula (III-1a), the formula (III-1b), the formula (III-1c) and/or the formula (III-1d) or a salt thereof, comprising reacting a compound represented by the formula (Ia) or (Ib) or a salt thereof, wherein ring W is a ring represented by the formula:

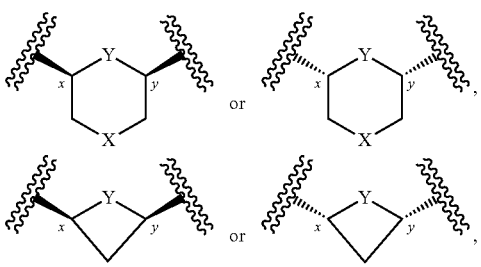

wherein each symbol is as defined above (e.g., piperidine ring, cyclopropane ring, cyclopentane ring, cyclohexane ring, a cyclohexene ring), each of which is optionally further substituted by 1 to 3 substituents selected from a $C_{1-6}$ alkyl group (e.g., methyl) optionally substituted by 1 to 3 $C_{6-14}$ aryl groups (e.g., phenyl), a $C_{1-6}$ alkyl-carbonyl group (e.g., acetyl) optionally substituted by 1 to 3 halogen atoms (e.g., fluorine atom), a $C_{1-6}$ alkoxy-carbonyl group (e.g., tertiary-butoxycarbonyl) and a $C_{6-14}$ arylsulfonyl group (e.g., phenylsulfonyl) optionally substituted by nitro), with a compound represented by the formula (II) or a salt thereof wherein $R^1$ and $R^2$ of the formula (II) are each independently a hydrogen atom, a $C_{1-5}$ alkyl group (e.g., methyl, ethyl, butyl) optionally substituted by $C_{1-6}$ alkoxy group (e.g., methoxy) or a $C_{1-6}$ alkoxy group (e.g., methoxy), in the presence of an aluminum compound selected from alkylaluminum and DIBAL, and cinchona alkaloid (e.g., quinine, quinidine, hydroquinine, hydroquinidine, cinchonine, cinchonidine).

(Production Method B2)

A production method of a compound represented by the formula (III-1a), the formula (III-1b), the formula (III-1c) and/or the formula (III-1d) or a salt thereof, wherein, in the aforementioned production method B1, ring W is a ring represented by the formula:

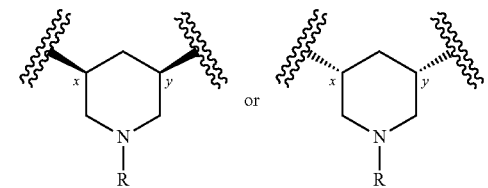

wherein each symbol is as defined above (i.e., piperidine ring), the aluminum compound is DIBAL, and cinchona alkaloid is selected from quinine, quinidine, hydroquinine and hydroquinidine.

(Production Method C1)

A production method of a compound represented by the formula (III-1a), the formula (III-1b), the formula (III-1c) and/or the formula (III-1d) or a salt thereof, comprising reacting a compound represented by the formula (Ia) or (Ib) or a salt thereof, wherein ring W is a ring represented by the formula:

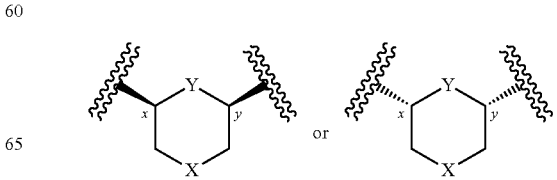

-continued

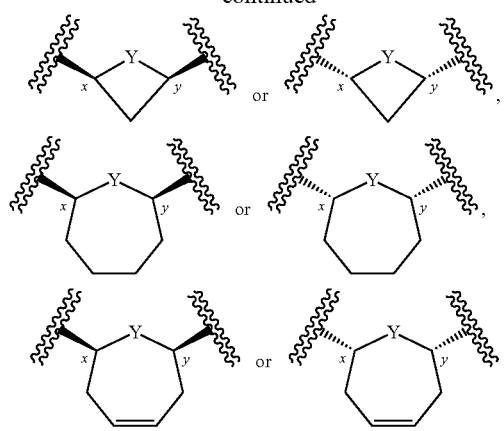

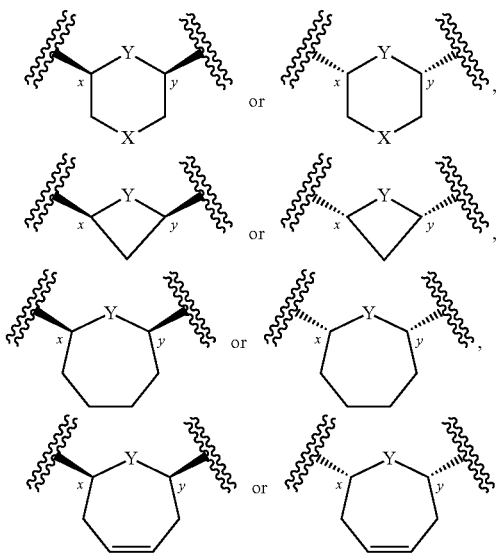

wherein each symbol is as defined above (e.g., piperidine ring, cyclopropane ring, cyclopentane ring, cyclohexane ring, a cyclohexene ring), each of which is optionally further substituted by 1 to 3 substituents selected from an optionally substituted $C_{1-6}$ alkyl group (e.g., methyl), an optionally substituted $C_{1-6}$ alkyl-carbonyl group (e.g., acetyl), an optionally substituted $C_{1-6}$ alkoxy-carbonyl group (e.g., tertiary-butoxycarbonyl) and an optionally substituted $C_{6-14}$ arylsulfonyl group (e.g., phenylsulfonyl), with a compound represented by the formula (II) or a salt thereof wherein $R^1$ and $R^2$ of the formula (II) are bonded to each other to form a non-aromatic heterocycle (e.g., pyrrolidine ring, piperidine ring, morpholine ring, thiomorpholine ring), in the presence of an aluminum compound selected from alkylaluminum and DIBAL, and cinchona alkaloid (e.g., quinine, quinidine, hydroquinine, hydroquinidine, cinchonine, cinchonidine).

(Production Method C2)

A production method of a compound represented by the formula (III-1a), the formula (III-1b), the formula (III-1c) and/or the formula (III-1d) or a salt thereof, wherein, in the aforementioned production method C1, ring W is a ring represented by the formula:

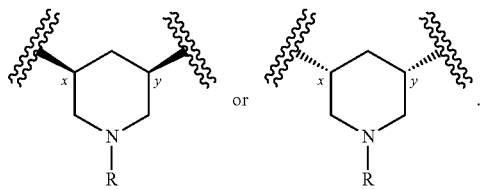

wherein each symbol is as defined above (i.e., piperidine ring), the aluminum compound is DIBAL, and cinchona alkaloid is selected from quinine, quinidine, hydroquinine and hydroquinidine.

(Production Method D1)

A production method of a compound represented by the formula (III-1a), the formula (III-1b), the formula (III-1c) and/or the formula (III-1d) or a salt thereof, comprising reacting a compound represented by the formula (Ia) or (Ib) or a salt thereof, wherein ring W is a ring represented by the formula:

wherein each symbol is as defined above (e.g., piperidine ring, cyclopropane ring, cyclopentane ring, cyclohexane ring, a cyclohexene ring), each of which is optionally further substituted by 1 to 3 substituents selected from a $C_{1-6}$ alkyl group (e.g., methyl) optionally substituted by 1 to 3 $C_{6-14}$ aryl groups (e.g., phenyl), a $C_{1-6}$ alkyl-carbonyl group (e.g., acetyl) optionally substituted by 1 to 3 halogen atoms (e.g., fluorine atom), a $C_{1-6}$ alkoxy-carbonyl group (e.g., tertiary-butoxycarbonyl) and a $C_{6-14}$ arylsulfonyl group (e.g., phenylsulfonyl) optionally substituted by nitro, with a compound represented by the formula (II) or a salt thereof wherein $R^1$ and $R^2$ of the formula (II) are bonded to each other to form a pyrrolidine ring, a piperidine ring, a morpholine ring or a thiomorpholine ring, in the presence of an aluminum compound selected from alkylaluminum and DIBAL, and cinchona alkaloid (e.g., quinine, quinidine, hydroquinine, hydroquinidine, cinchonine, cinchonidine).

(Production Method D2)

A production method of a compound represented by the formula (III-1a), the formula (III-1b), the formula (III-1c) and/or the formula (III-1d) or a salt thereof, wherein, in the aforementioned production method D1, ring W is a ring represented by the formula:

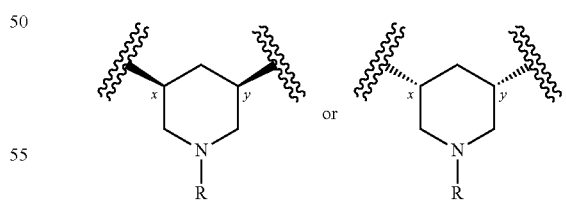

wherein each symbol is as defined above (i.e., piperidine ring), the aluminum compound is DIBAL, and
cinchona alkaloid is selected from quinine, quinidine, hydroquinine and hydroquinidine.

(Production Method E)

A production method of (3S,5R)-1-(tertiary-butoxycarbonyl)-5-(morpholin-4-ylcarbonyl)piperidine-3-carboxylic acid or a salt thereof, comprising reacting tertiary-butyl 2,4-dioxo-3-oxa-7-azabicyclo[3.3.1]nonane-7-carboxylate or a salt thereof, with morpholine in the presence of an aluminum compound and a chiral amine compound.

A compound represented by the formula (III-1a), the formula (III-1b), the formula (III-1c) and/or the formula (III-1d), wherein ring W is a ring represented by the formula:

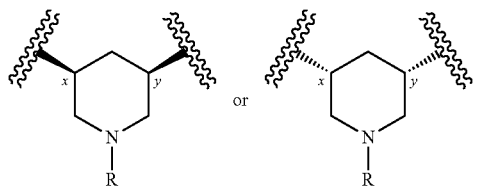

wherein R is tertiary-butoxycarbonyl, and other symbols are as defined above, is a novel compound.

The present invention also relates to a production method of 1-(4-methoxybutyl)-N-(2-methylpropyl)-N-[(3S,5R)-5-(morpholin-4-ylcarbonyl)piperidin-3-yl]-1H-benzimidazole-2-carboxamide or a salt thereof.

1-(4-Methoxybutyl)-N-(2-methylpropyl)-N-[(3S,5R)-5-(morpholin-4-ylcarbonyl)piperidin-3-yl]-1H-benzimidazole-2-carboxamide or a salt thereof can be produced from (3S,5R)-1-(tertiary-butoxycarbonyl)-5-(morpholin-4-ylcarbonyl)piperidine-3-carboxylic acid or a salt thereof as a starting compound, and according to a method known per se (e.g., the methods described in WO 2009/154300, WO 2011/158880 and the like). Specifically, the production method comprises
A) a step of producing (3S,5R)-1-(tertiary-butoxycarbonyl)-5-(morpholin-4-ylcarbonyl)piperidine-3-carboxylic acid or a salt thereof by reacting tertiary-butyl 2,4-dioxo-3-oxa-7-azabicyclo[3.3.1]nonane-7-carboxylate or a salt thereof with morpholine in the presence of an aluminum compound and a chiral amine compound; and optionally further comprises
B) a step of producing (3S,5R)-tertiary-butyl 3-[(2-methylpropyl)amino]-5-(morpholin-4-ylcarbonyl)piperidine-1-carboxylate or a salt thereof by amidating a carboxyl group of (3S,5R)-1-(tertiary-butoxycarbonyl)-5-(morpholin-4-ylcarbonyl)piperidine-3-carboxylic acid or a salt thereof; and further
C) a step of producing (3S,5R)-tertiary-butyl 3-[{[1-(4-methoxybutyl)-1H-benzimidazol-2-yl]carbonyl}(2-methylpropyl)amino]-5-(morpholin-4-ylcarbonyl)piperidine-1-carboxylate or a salt thereof by reacting (3S,5R)-tertiary-butyl 3-[(2-methylpropyl)amino]-5-(morpholin-4-ylcarbonyl)piperidine-1-carboxylate or a salt thereof with 1-(4-methoxybutyl)-2-trichloromethyl-1H-benzimidazole or a salt thereof; and further
D) a deprotection step of (3S,5R)-tertiary-butyl 3-[{[1-(4-methoxybutyl)-1H-benzimidazol-2-yl]carbonyl}(2-methylpropyl)amino]-5-(morpholin-4-ylcarbonyl)piperidine-1-carboxylate or a salt thereof.

EXAMPLES

The present invention is further explained in detail by referring to the following Reference Examples and Examples which are mere working examples not to be construed as limitative and may be changed without departing from the scope of the present invention.

The term "room temperature" in the following Reference Examples and Examples indicates the range of generally from about 10° C. to about 35° C. The optical purity (asymmetric yield) of optically active forms was evaluated according to enantiomeric excess (% ee). The enantiomeric excess was determined by the following formula:

enantiomeric excess (% ee)=100×[(R)−(S)]/[(R)+(S)]
or 100×[(S)−(R)]/[(R)+(S)]

wherein (R) and (S) are each an area of each enantiomer in high performance liquid chromatography (HPLC).

The solvent used for chromatography is in % by volume and other "%" is in % by weight.

OH proton, NH proton etc. that could not be confirmed due to broad peak by proton NMR spectrum are not included in the data.

The other symbols used herein mean the following:
s: singlet
d: doublet
t: triplet
q: quartet
m: multiplet
br: broad
br. s.: broad singlet
dd: double doublet
dt: double triplet
dq: double quartet
td: triple doublet
tt: triple triplet
ddt: double double triplet
J: coupling constant
Hz: Hertz
DMSO-$d_6$: deuterated dimethyl sulfoxide
$^1$H NMR: proton nuclear magnetic resonance In the following Reference Examples and Examples, nuclear magnetic resonance spectrum (NMR) was measured under the following conditions.

$^1$H nuclear magnetic resonance spectrum ($^1$H NMR): DPX300 (300 MHz) manufactured by Bruker or BRUKER AVANCE 500 (500 MHz) manufactured by Bruker, internal standard substance: tetramethylsilane Reference Example 1

3-oxabicyclo[3.3.1]nonane-2,4-dione

To a reaction vessel were added (1R,3S)-cyclohexane-1,3-dicarboxylic acid (10 g) and THF (20 mL), and the mixture was cooled to 5° C. Trifluoroacetic anhydride (8.19 mL) was added dropwise, and the mixture was stirred for about 1 hr. The reaction mixture was warmed to room temperature, heptane (20 mL) was added, and the mixture was cooled to 5° C. and stirred for about 30 min. The precipitate was collected by filtration, and washed with heptane to give the title compound. yield (6.7 g)

Reference Example 2

(3S,5R)-tertiary-butyl 3-(isobutylamino)-5-(morpholine-4-carbonyl)piperidine-1-carboxylate succinate In a reaction vessel were charged THF (240 mL), (3S,5R)-1-(tertiary-butoxycarbonyl)-5-(morpholine-4-carbonyl)piperidine-3-carboxylic acid (20.0 g), triethylamine (12.2 mL) and diphenylphosphoryl azide (15.1 mL), and the mixture was reacted at 60° C. for 1 hr and cooled to 25° C. Separately, in a reaction vessel were charged THF (60 mL) and sodium trimethylsilanolate (19.7 g), the mixture was cooled to 0° C., the reaction mixture reacted earlier was added dropwise thereto over about 1 hr, and the mixture was reacted at 0° C. for 0.5 hr. Acetic acid (40 mL) was slowly added dropwise at 0° C. and, after stirring for 10 min, ethanol (60 mL) and isobutylaldehyde (5.3 mL) were added at 25° C., and the mixture was stirred for 10 min. Then, sodium borohydride (1.88 g) was added and, after stirring for 30 min, sodium borohydride (1.88 g) was further added at 25° C., and the mixture was stirred for 30 min. After completion of the reaction, water (100 mL) was added, and the mixture was stirred at room temperature for 10 min. The organic layer was concentrated, toluene (140 mL) and 5N aqueous sodium hydroxide solution (120 mL) were slowly added dropwise, and the mixture was separated. The organic layer was washed with 1N aqueous sodium hydroxide solution (100 mL), and washed again with 1N aqueous sodium hydroxide solution (100 mL). The aqueous layers were combined, and extracted with toluene (100 mL). The organic layers were combined, washed with 10 w/v % brine (100 mL), and concentrated. Ethanol (100 mL) was added, and the mixture was concentrated under reduced pressure to about 60 mL, ethyl acetate (40 mL) was added and the mixture was heated to 60° C. Succinic acid (6.9 g) was added, and the mixture was stirred for 30 min. Ethyl acetate (200 mL) was added dropwise at 60° C., and the mixture was stirred for 30 min. After stirring at room temperature for 1 hr, the mixture was stirred at 0° C. for 1 hr. The crystal was collected by filtration, and washed with mixed a solution (60 mL) of ethyl acetate/normal heptane (6/1). The obtained crystals were dried under reduced pressure at an outer temperature of 50° C. to a constant weight to give the title compound as almost white crystals. yield (22.8 g)

Example 1

(3S,5R)-1-(tertiary-butoxycarbonyl)-5-(morpholin-4-ylcarbonyl)piperidine-3-carboxylic acid To a reaction vessel were added chlorobenzene (7.5 mL) and quinine (0.70 g), the mixture was stirred, and DIBAL 1.0M hexane solution (2.16 mL) was added dropwise. The reaction mixture was cooled to −40° C., tertiary-butyl 2,4-dioxo-3-oxa-7-azabicyclo[3.3.1]nonane-7-carboxylate (0.50 g) was added, and the mixture was stirred for about 1 hr. To another reaction vessel were added chlorobenzene (2.5 mL) and morpholine (0.17 mL), and the obtained solution was cooled to −40° C. and added dropwise to the earlier reaction solution. After completion of the reaction, the mixture was separated with ethyl acetate and 10 w/w % aqueous citric acid solution, and the obtained aqueous layer was extracted again with ethyl acetate. The organic layers were combined, washed with 10 w/w % brine, and concentrated to give the title compound.

$^1$H NMR (500 MHz, DMSO-$d_6$) δ ppm 1.41 (s, 9H), 1.47-1.72 (m, 1H), 1.89-2.10 (m, 1H), 2.36-2.49 (m, 1H), 2.55-2.83 (m, 3H), 3.40-3.50 (m, 2H), 3.51-3.57 (m, 4H), 3.59 (br. s., 2H), 3.83-4.04 (m, 1H), 4.05-4.29 (m, 1H), 12.52 (s, 1H)
optical purity 94.3% ee
<HPLC Analysis Conditions>
column: CHIRALPAK IC (manufactured by Daicel Corporation)
column temperature: constant temperature near 15° C.
mobile phase: Solution A) 0.02 mol/L $KH_2PO_4$ buffer (pH 3.0):acetonitrile=70:30
Solution B) 0.02 mol/L $KH_2PO_4$ buffer (pH 3.0):acetonitrile=50:50
Gradient Program

TABLE 1

| time (min) | Solution A (%) | Solution B (%) |
|---|---|---|
| 0 | 100 | 0 |
| 17 | 100 | 0 |
| 21 | 0 | 100 |
| 32 | 0 | 100 |
| 32.1 | 100 | 0 |
| 37 | 100 | 0 | flow: 0.5 mL/min
retention time: (3R,5S) form 13.8 min, (3S,5R) form 15.5 min

In the same manner as in Example 1 and using the corresponding acid anhydride and amine, the compounds of the following Examples 2-9 were synthesized.

Example 2

(3S,5R)-1-(tertiary-butoxycarbonyl)-5-(diethylcarbamoyl)piperidine-3-carboxylic acid (acid anhydride: tertiary-butyl 2,4-dioxo-3-oxa-7-azabicyclo[3.3.1]nonane-7-carboxylate; amine: diethylamine)
$^1$H NMR (500 MHz, DMSO-$d_6$) δ ppm 1.00 (t, J=7.09 Hz, 3H), 1.13 (t, J=6.94 Hz, 3H), 1.40 (s, 9H), 1.64 (d, J=11.66 Hz, 1H), 1.93-2.04 (m, 1H), 2.42-2.49 (m, 1H), 2.57-2.68 (m, 2H), 2.68-2.84 (m, 1H), 3.20 (br. s., 1H), 3.26-3.30 (m, 1H), 3.43 (br. s., 1H), 3.78-4.00 (m, 1H), 4.07-4.29 (m, 1H), 12.46 (br. s., 1H)
optical purity 53.1% ee
<HPLC Analysis Conditions>
column: CHIRALPAK IE (manufactured by Daicel Corporation)
column temperature: constant temperature near 15° C.
mobile phase: Solution A) 0.02 mol/L $KH_2PO_4$ buffer (pH 3.0):acetonitrile=70:30
Solution B) 0.02 mol/L $KH_2PO_4$ buffer (pH 3.0):acetonitrile=50:50
Gradient Program

TABLE 2

| time (min) | Solution A (%) | Solution B (%) |
|---|---|---|
| 0 | 100 | 0 |
| 10 | 100 | 0 |
| 13 | 0 | 100 |
| 28 | 0 | 100 |
| 28.1 | 100 | 0 |
| 35 | 100 | 0 | flow: 0.5 mL/min
retention time: (3R,5S) form 21.3 min, (3S,5R) form 22.2 min

Example 3

(3S,5R)-1-(tertiary-butoxycarbonyl)-5-(piperidin-1-ylcarbonyl)piperidine-3-carboxylic acid (acid anhydride: tertiary-butyl 2,4-dioxo-3-oxa-7-azabicyclo[3.3.1]nonane-7-carboxylate; amine: piperidine)
$^1$H NMR (500 MHz, DMSO-$d_6$) δ ppm 1.40 (s, 11H), 1.51 (d, J=4.41 Hz, 2H), 1.59 (d, J=5.04 Hz, 3H), 1.99 (d, J=12.93

Hz, 1H), 2.40-2.49 (m, 1H), 2.54-2.82 (m, 3H), 3.36 (br. s., 1H), 3.41-3.67 (m, 3H), 3.91 (br. s., 1H), 4.15 (br. s., 1H), 12.48 (br. s., 1H)

optical purity 76.7% ee

<HPLC Analysis Conditions> column: CHIRALPAK IE (manufactured by Daicel Corporation)

column temperature: constant temperature near 15° C.

mobile phase: Solution A) 0.02 mol/L $KH_2PO_4$ buffer (pH 3.0):acetonitrile=70:30

Solution B) 0.02 mol/L $KH_2PO_4$ buffer (pH 3.0):acetonitrile=50:50

Gradient Program

TABLE 3

| time (min) | Solution A (%) | Solution B (%) |
|---|---|---|
| 0 | 100 | 0 |
| 1 | 100 | 0 |
| 35 | 70 | 30 |
| 39 | 70 | 30 |
| 49 | 0 | 100 |
| 49.1 | 0 | 100 |
| 55 | 100 | 0 | flow: 0.5 mL/min retention time: (3R,5S) form 23.7 min, (3S,5R) form 25.8 min

Example 4

(3S,5R)-1-(tertiary-butoxycarbonyl)-5-(pyrrolidin-1-ylcarbonyl)piperidine-3-carboxylic acid (acid anhydride: tertiary-butyl 2,4-dioxo-3-oxa-7-azabicyclo[3.3.1]nonane-7-carboxylate; amine: tetrahydropyrrole)

$^1$H NMR (500 MHz, DMSO-$d_6$) δ ppm 1.41 (s, 9H), 1.60 (q, J=12.30 Hz, 1H), 1.78 (t, J=6.78 Hz, 2H), 1.89 (t, J=6.78 Hz, 2H), 2.05 (d, J=12.93 Hz, 1H), 2.40 (tt, J=12.06, 3.86 Hz, 1H), 2.53-2.73 (m, 3H), 3.28 (t, J=6.78 Hz, 2H), 3.40-3.60 (m, 2H), 3.97 (br. s., 1H), 4.15 (br. s., 1H), 12.48 (br. s., 1H)

optical purity 62.4% ee

<HPLC Analysis Conditions> column: CHIRALPAK IC (manufactured by Daicel Corporation)

column temperature: constant temperature near 15° C.

mobile phase: Solution A) 0.02 mol/L $KH_2PO_4$ buffer (pH 3.0):acetonitrile=70:30

Solution B) 0.02 mol/L $KH_2PO_4$ buffer (pH 3.0):acetonitrile=50:50

Gradient Program

TABLE 4

| time (min) | Solution A (%) | Solution B (%) |
|---|---|---|
| 0 | 100 | 0 |
| 20 | 100 | 0 |
| 23 | 0 | 100 |
| 34 | 0 | 100 |
| 34.1 | 100 | 0 |
| 38 | 100 | 0 | flow: 0.5 mL/min retention time: (3R,5S) form 20.4 min, (3S,5R) form 26.2 min

Example 5

(3S,5R)-1-(tertiary-butoxycarbonyl)-5-[methoxy(methyl)carbamoyl]piperidine-3-carboxylic acid (acid anhydride: tertiary-butyl 2,4-dioxo-3-oxa-7-azabicyclo[3.3.1]nonane-7-carboxylate; amine: N,O-dimethylhydroxylamine hydrochloride)

$^1$H NMR (500 MHz, DMSO-$d_6$) δ ppm 1.41 (s, 9H), 1.60 (q, J=11.77 Hz, 1H), 2.04-2.10 (m, 1H), 2.36-2.46 (m, 1H), 2.56-2.73 (m, 2H), 2.80 (br. s., 1H), 3.11 (br. s., 3H), 3.71 (s, 3H), 4.04 (d, J=9.14 Hz, 1H), 4.16 (br. s., 1H), 12.50 (br. s., 1H)

optical purity 25.6% ee

<HPLC Analysis Conditions> column: CHIRALPAK IC (manufactured by Daicel Corporation)

column temperature: constant temperature near 15° C.

mobile phase: Solution A) 0.02 mol/L $KH_2PO_4$ buffer (pH 3.0):acetonitrile=70:30

Solution B) 0.02 mol/L $KH_2PO_4$ buffer (pH 3.0):acetonitrile=50:50

Gradient Program

TABLE 5

| time (min) | Solution A (%) | Solution B (%) |
|---|---|---|
| 0 | 100 | 0 |
| 20 | 100 | 0 |
| 23 | 0 | 100 |
| 34 | 0 | 100 |
| 34.1 | 100 | 0 |
| 38 | 100 | 0 | flow: 0.5 mL/min retention time: (3R,5S) form 15.3 min, (3S,5R) form 18.0 min

Example 6

(3S,5R)-1-(tertiary-butoxycarbonyl)-5-[(2-methoxyethyl)(methyl)carbamoyl]piperidine-3-carboxylic acid (acid anhydride: tertiary-butyl 2,4-dioxo-3-oxa-7-azabicyclo[3.3.1]nonane-7-carboxylate; amine: N-(2-methoxyethyl)methylamine)

$^1$H NMR (500 MHz, DMSO-$d_6$) δ ppm 1.41 (s, 9H), 1.50-1.70 (m, 1H), 1.98-2.06 (m, 1H), 2.38-2.47 (m, 1H), 2.55-2.79 (m, 3H), 2.80-3.11 (m, 3H), 3.26 (d, J=19.86 Hz, 3H), 3.38-3.44 (m, 2H), 3.46 (s, 2H), 3.55-3.72 (m, 1H), 3.80-4.01 (m, 1H), 4.05-4.36 (m, 1H), 12.47 (s, 1H)

optical purity 78.4% ee

<HPLC Analysis Conditions>
column: CHIRALPAK IC (manufactured by Daicel Corporation)
column temperature: constant temperature near 15° C.
mobile phase: Solution A) 0.02 mol/L $KH_2PO_4$ buffer (pH 3.0):acetonitrile=70:30
Solution B) 0.02 mol/L $KH_2PO_4$ buffer (pH 3.0):acetonitrile=50:50
Gradient Program

TABLE 6

| time (min) | Solution A (%) | Solution B (%) |
| --- | --- | --- |
| 0 | 100 | 0 |
| 17 | 100 | 0 |
| 21 | 0 | 100 |
| 32 | 0 | 100 |
| 32.1 | 100 | 0 |
| 37 | 100 | 0 | flow: 0.5 mL/min
retention time: (3R,5S) form 13.7 min, (3S,5R) form 16.8 min

Example 7

(3S,5R)-1-(tertiary-butoxycarbonyl)-5-[(2-methoxyethyl)carbamoyl]piperidine-3-carboxylic acid (acid anhydride: tertiary-butyl 2,4-dioxo-3-oxa-7-azabicyclo[3.3.1]nonane-7-carboxylate; amine: 2-methoxyethylamine)
$^1$H NMR (500 MHz, DMSO-$d_6$) δ ppm 1.41 (s, 9H), 1.52-1.63 (m, 1H), 2.07 (d, J=12.93 Hz, 1H), 2.25-2.34 (m, 2H), 2.53-2.80 (m, 2H), 3.21 (br. s., 2H), 3.25 (s, 3H), 3.31-3.36 (m, 2H), 3.97 (br. s., 1H), 4.14 (br. s., 1H), 8.02 (t, J=5.36 Hz, 1H), 12.50 (br. s., 1H)
optical purity 26.1% ee
<HPLC Analysis Conditions>
column: CHIRALPAK IC (manufactured by Daicel Corporation)
column temperature: constant temperature near 15° C.
mobile phase: Solution A) 0.02 mol/L $KH_2PO_4$ buffer (pH 3.0):acetonitrile=70:30
Solution B) 0.02 mol/L $KH_2PO_4$ buffer (pH 3.0):acetonitrile=50:50
Gradient Program

TABLE 7

| time (min) | Solution A (%) | Solution B (%) |
| --- | --- | --- |
| 0 | 100 | 0 |
| 10 | 100 | 0 |
| 13 | 0 | 100 |
| 28 | 0 | 100 |
| 28.1 | 100 | 0 |
| 35 | 100 | 0 | flow: 0.5 mL/min
retention time: (3S,5R) form 9.3 min, (3R,5S) form 9.9 min

Example 8

(3S,5R)-1-(tertiary-butoxycarbonyl)-5-(butylcarbamoyl)piperidine-3-carboxylic acid (acid anhydride: tertiary-butyl 2,4-dioxo-3-oxa-7-azabicyclo[3.3.1]nonane-7-carboxylate; amine: normal butylamine)
$^1$H NMR (500 MHz, DMSO-$d_6$) δ ppm 0.86 (t, J=7.25 Hz, 3H), 1.26 (d, J=7.57 Hz, 2H), 1.33-1.39 (m, 2H), 1.40 (s, 9H), 1.49-1.65 (m, 1H), 2.06 (d, J=12.61 Hz, 1H), 2.17-2.33 (m, 2H), 2.53-2.81 (m, 2H), 2.91-3.13 (m, 2H), 3.32 (br. s., 5H), 3.82-4.04 (m, 1H), 4.05-4.31 (m, 1H), 7.89 (t, J=5.5 Hz, 1H), 12.50 (br. s., 1H)
optical purity 30.8% ee
<HPLC Analysis Conditions>
column: CHIRALPAK IE (manufactured by Daicel Corporation)
column temperature: constant temperature near 15° C.
mobile phase: Solution A) 0.02 mol/L $KH_2PO_4$ buffer (pH 3.0):acetonitrile=70:30
Solution B) 0.02 mol/L $KH_2PO_4$ buffer (pH 3.0):acetonitrile=50:50
Gradient Program

TABLE 8

| time (min) | Solution A (%) | Solution B (%) |
| --- | --- | --- |
| 0 | 100 | 0 |
| 27 | 100 | 0 |
| 31 | 0 | 100 |
| 40 | 0 | 100 |
| 40.1 | 100 | 0 |
| 45 | 100 | 0 | flow: 0.5 mL/min
retention time: (3S,5R) form 24.4 min, (3R,5S) form 27.5 min

Example 9

(3S,5R)-1-(tertiary-butoxycarbonyl)-5-(thiomorpholin-4-ylcarbonyl)piperidine-3-carboxylic acid (acid anhydride: tertiary-butyl 2,4-dioxo-3-oxa-7-azabicyclo[3.3.1]nonane-7-carboxylate; amine: thiomorpholine)
$^1$H NMR (500 MHz, DMSO-$d_6$) δ ppm 1.41 (s, 9H), 1.48-1.70 (m, 1H), 1.95-2.08 (m, 1H), 2.42-2.50 (m, 1H), 2.55 (br. s., 2H), 2.58-2.83 (m, 5H), 3.60-3.72 (m, 1H), 3.72-3.85 (m, 3H), 3.86-4.00 (m, 1H), 4.05-4.29 (m, 1H), 12.51 (br. s., 1H)
optical purity 90.9% ee
<HPLC Analysis Conditions>
column: CHIRALPAK IC (manufactured by Daicel Corporation)
column temperature: constant temperature near 15° C.
mobile phase: Solution A) 0.02 mol/L $KH_2PO_4$ buffer (pH 3.0):acetonitrile=70:30
Solution B) 0.02 mol/L $KH_2PO_4$ buffer (pH 3.0):acetonitrile=50:50
Gradient Program

TABLE 9

| time (min) | Solution A (%) | Solution B (%) |
| --- | --- | --- |
| 0 | 100 | 0 |
| 1 | 100 | 0 |
| 4 | 0 | 100 |
| 19 | 0 | 100 |
| 19.1 | 100 | 0 |
| 25 | 100 | 0 | flow: 0.5 mL/min
retention time: (3R,5S) form 14.5 min, (3S,5R) form 16.1 min

Example 10

(3S,5R)-1-(tertiary-butoxycarbonyl)-5-(morpholin-4-ylcarbonyl)piperidine-3-carboxylic acid To a reaction vessel were added chlorobenzene (7.5 mL) and quinine (0.70 g), the mixture was stirred, and trimethylaluminum 1.4M toluene solution (1.54 mL) was added dropwise. The reaction mixture was cooled to −40° C., tertiary-butyl 2,4-dioxo-3-oxa-7-azabicyclo[3.3.1]nonane-7-carboxylate (0.50 g) was added, and the mixture was stirred for about 1 hr. To another reaction vessel were added chlorobenzene (2.5 mL) and morpholine (0.17 mL), the obtained solution was cooled to −40° C., and added dropwise to the earlier reaction solution. After completion of the reaction, the mixture was separated with ethyl acetate and 10 w/w % aqueous citric acid solution, and the obtained aqueous layer was extracted again with ethyl acetate. The organic layers were combined, washed with 10 w/w % brine, and concentrated to give the title compound.
optical purity 82.1% ee

Example 11

(1R,2S)-2-(diethylcarbamoyl)cyclohexanecarboxylic acid

To a reaction vessel were added chlorobenzene (7.5 mL) and quinine (0.70 g), the mixture was stirred, and DIBAL 1.0M hexane solution (2.16 mL) was added dropwise. To this reaction mixture was added diethylamine (0.20 mL), and the mixture was stirred for about 2 hr. The reaction mixture was cooled to −10° C., and cis-1,2-cyclohexanedicarboxylic acid anhydride (0.50 g) was added. After completion of the reaction, the mixture was separated with ethyl acetate and 10 w/w % aqueous citric acid solution, and the obtained aqueous layer was extracted again with ethyl acetate. The organic layers were combined, washed with 10 w/w % brine, and concentrated to give the title compound.
$^1$H NMR (500 MHz, DMSO-d$_6$) δ ppm 0.97 (t, J=7.09 Hz, 3H), 1.11-1.16 (m, 3H), 1.26-1.46 (m, 3H), 1.49-1.55 (m, 1H), 1.66-1.82 (m, 3H), 2.15-2.26 (m, 1H), 2.38 (dt, J=10.64, 4.45 Hz, 1H), 3.07 (dd, J=13.56, 6.94 Hz, 1H), 3.15 (q, J=4.73 Hz, 1H), 3.24 (dd, J=14.66, 7.09 Hz, 1H), 3.35 (dq, J=14.03, 6.99 Hz, 2H), 12.00 (br. s., 1H)
optical purity 13.7% ee
<HPLC Analysis Conditions>
column: CHIRALPAK IF (manufactured by Daicel Corporation)
column temperature: constant temperature near 15° C.
mobile phase: Solution A) 0.02 mol/L KH$_2$PO$_4$ buffer (pH 3.0):acetonitrile=70:30
Solution B) 0.02 mol/L KH$_2$PO$_4$ buffer (pH 3.0):acetonitrile=50:50
Gradient Program

TABLE 10

| time (min) | Solution A (%) | Solution B (%) |
|---|---|---|
| 0 | 100 | 0 |
| 3 | 80 | 20 |
| 16 | 80 | 20 |
| 22 | 20 | 80 |
| 32 | 20 | 80 |
| 32.1 | 100 | 0 |
| 40 | 100 | 0 | flow: 0.5 mL/min
retention time: (1R,2S) form 22.3 min, (1S,2R) form 29.7 min

In the same manner as in Example 11 and using the corresponding acid anhydride and amine, the compounds of the following Examples 12-20 were synthesized.

Example 12

(1R,6S)-6-(diethylcarbamoyl)cyclohex-3-ene-1-carboxylic acid (acid anhydride: cis-4-tetrahydrophthalic acid anhydride; amine: diethylamine)
$^1$H NMR (500 MHz, DMSO-d$_6$) δ ppm 0.98 (t, J=6.94 Hz, 3H), 1.10-1.18 (m, 3H), 2.10-2.18 (m, 1H), 2.18-2.26 (m, 1H), 2.28-2.36 (m, 1H), 2.61-2.68 (m, 2H), 3.17 (dt, J=13.64, 6.90 Hz, 1H), 3.20-3.26 (m, 1H), 3.26-3.38 (m, 3H), 5.55-5.61 (m, 1H), 5.61-5.69 (m, 1H), 12.32 (br. s., 1H)
optical purity 1.9% ee
<HPLC Analysis Conditions>
column: CHIRALPAK IF (manufactured by Daicel Corporation)
column temperature: constant temperature near 15° C.
mobile phase: Solution A) 0.02 mol/L KH$_2$PO$_4$ buffer (pH 3.0):acetonitrile=70:30
Solution B) 0.02 mol/L KH$_2$PO$_4$ buffer (pH 3.0):acetonitrile=50:50
Gradient Program

TABLE 11

| time (min) | Solution A (%) | Solution B (%) |
|---|---|---|
| 0 | 100 | 0 |
| 3 | 80 | 20 |
| 16 | 80 | 20 |
| 22 | 20 | 80 |
| 32 | 20 | 80 |
| 32.1 | 100 | 0 |
| 40 | 100 | 0 | flow: 0.5 mL/min
retention time: (1S,6R) form 24.1 min, (1R,6S) form 31.6 min

Example 13

(1S,2R)-2-(diethylcarbamoyl)cyclopropanecarboxylic acid (acid anhydride: 3-oxabicyclo[3.1.0]hexane-2,4-dione; amine:diethylamine)
$^1$H NMR (500 MHz, DMSO-d$_6$) δ ppm 0.95 (t, J=7.09 Hz, 3H), 1.05-1.15 (m, 4H), 1.34 (td, J=6.46, 3.78 Hz, 1H), 1.94 (td, J=8.59, 6.46 Hz, 1H), 2.08-2.18 (m, 1H), 3.07-3.19 (m, 1H), 3.27-3.40 (m, 2H), 3.53 (dq, J=14.50, 7.25 Hz, 1H), 12.37 (br. s., 1H)
optical purity 15.7% ee
<HPLC Analysis Conditions>
column: CHIRALPAK IA-3 (manufactured by Daicel Corporation)

column temperature: constant temperature near 15° C.
mobile phase: Solution A) 0.02 mol/L $KH_2PO_4$ buffer (pH 3.0):acetonitrile=70:30
Solution B) 0.02 mol/L $KH_2PO_4$ buffer (pH 3.0):acetonitrile=50:50
Gradient Program

TABLE 12

| time (min) | Solution A (%) | Solution B (%) |
|---|---|---|
| 0 | 100 | 0 |
| 3 | 80 | 20 |
| 16 | 80 | 20 |
| 22 | 20 | 80 |
| 32 | 20 | 80 |
| 32.1 | 100 | 0 |
| 40 | 100 | 0 | flow: 0.5 mL/min
retention time: (1R,2S) form 7.8 min, (1S,2R) form 8.1 min

Example 14

(1R,3S)-3-(diethylcarbamoyl)cyclohexanecarboxylic acid (acid anhydride: 3-oxabicyclo[3.3.1]nonane-2,4-dione; amine:diethylamine)
$^1$H NMR (500 MHz, DMSO-$d_6$) δ ppm 0.99 (t, J=7.09 Hz, 3H), 1.11 (t, J=7.09 Hz, 3H), 1.19-1.38 (m, 3H), 1.38-1.46 (m, 1H), 1.59 (d, J=12.61 Hz, 1H), 1.73-1.81 (m, 2H), 1.84-1.91 (m, 1H), 2.32 (tt, J=12.41, 3.51 Hz, 1H), 2.52-2.58 (m, 1H), 3.20-3.36 (m, 4H), 12.05 (s, 1H)
optical purity 50.9% ee
<HPLC Analysis Conditions>
column: CHIRALPAK IF (manufactured by Daicel Corporation)
column temperature: constant temperature near 15° C.
mobile phase: Solution A) 0.02 mol/L $KH_2PO_4$ buffer (pH 3.0):acetonitrile=70:30
Solution B) 0.02 mol/L $KH_2PO_4$ buffer (pH 3.0):acetonitrile=50:50
Gradient Program

TABLE 13

| time (min) | Solution A (%) | Solution B (%) |
|---|---|---|
| 0 | 100 | 0 |
| 3 | 80 | 20 |
| 16 | 80 | 20 |
| 22 | 20 | 80 |
| 32 | 20 | 80 |
| 32.1 | 100 | 0 |
| 40 | 100 | 0 | flow: 0.5 mL/min
retention time: (1R,3S) form 13.5 min, (1S,3R) form 17.8 min

Example 15

(3S,5R)-5-(diethylcarbamoyl)-1-(trifluoroacetyl)piperidine-3-carboxylic acid (acid anhydride: 7-(2,2,2-trifluoroacetyl)-3-oxa-7-azabicyclo[3.3.1]nonane-2,4-dione; amine: diethylamine)
$^1$H NMR (500 MHz, DMSO-$d_6$) δ ppm 1.02 (td, J=7.01, 2.68 Hz, 3H), 1.08-1.18 (m, 3H), 1.64-1.77 (m, 1H), 2.03-2.12 (m, 1 H), 2.64-2.82 (m, 1H), 2.84-2.96 (m, 2H), 3.12-3.30 (m, 2H), 3.30-3.34 (m, 2H), 3.38-3.46 (m, 1H), 3.61-4.09 (m, 1H), 4.16-4.57 (m, 1H), 12.72 (br. s., 1H)
optical purity 26.0% ee
<HPLC Analysis Conditions>
column: CHIRALPAK IF (manufactured by Daicel Corporation)
column temperature: constant temperature near 15° C.
mobile phase: Solution A) 0.02 mol/L $KH_2PO_4$ buffer (pH 3.0):acetonitrile=70:30
Solution B) 0.02 mol/L $KH_2PO_4$ buffer (pH 3.0):acetonitrile=50:50
Gradient Program

TABLE 14

| time (min) | Solution A (%) | Solution B (%) |
|---|---|---|
| 0 | 100 | 0 |
| 3 | 80 | 20 |
| 16 | 80 | 20 |
| 22 | 20 | 80 |
| 32 | 20 | 80 |
| 32.1 | 100 | 0 |
| 40 | 100 | 0 | flow: 0.5 mL/min
retention time: (3S,5R) form 18.2 min, (3R,5S) form 20.3 min

Example 16

(3S,5R)-5-(diethylcarbamoyl)-1-tritylpiperidine-3-carboxylic acid (acid anhydride: 7-trityl-3-oxa-7-azabicyclo[3.3.1]nonane-2,4-dione; amine: diethylamine)
$^1$H NMR (500 MHz, DMSO-$d_6$) δ ppm 0.93 (t, J=7.09 Hz, 3H), 1.14 (t, J=7.09 Hz, 3H), 1.20-1.36 (m, 3H), 1.87-1.98 (m, 1H), 2.91-3.01 (m, 2H), 3.06 (dq, J=13.64, 6.91 Hz, 1H), 3.17 (tt, J=11.19, 3.47 Hz, 1H), 3.24-3.32 (m, 3H), 3.44-3.53 (m, 1H), 7.09-7.48 (m, 15H), 12.27 (br. s., 1H)
optical purity 24.6% ee
<HPLC Analysis Conditions>
column: CHIRALPAK IB (manufactured by Daicel Corporation)
column temperature: constant temperature near 15° C.
mobile phase: Solution A) 0.02 mol/L $KH_2PO_4$ buffer (pH 3.0):acetonitrile=70:30
Solution B) 0.02 mol/L $KH_2PO_4$ buffer (pH 3.0):acetonitrile=50:50
Gradient Program

TABLE 15

| time (min) | Solution A (%) | Solution B (%) |
|---|---|---|
| 0 | 100 | 0 |
| 5 | 0 | 100 |

TABLE 15-continued

| time (min) | Solution A (%) | Solution B (%) |
|---|---|---|
| 45 | 0 | 100 |
| 45.1 | 100 | 0 |
| 50 | 100 | 0 | flow: 0.5 mL/min
retention time: (3R,5S) form 35.0 min, (3S,5R) form 38.5 min

Example 17

(3S,5R)-5-(diethylcarbamoyl)-1-[(2-nitrophenyl)sulfonyl]piperidine-3-carboxylic acid (acid anhydride: 7-((2-nitrophenyl)sulfonyl)-3-oxa-7-azabicyclo[3.3.1]nonane-2,4-dione; amine: diethylamine)
$^1$H NMR (500 MHz, DMSO-$d_6$) δ ppm 1.01 (t, J=7.09 Hz, 3H), 1.12 (t, J=7.09 Hz, 3H), 1.53 (q, J=12.30 Hz, 1H), 1.99-2.09 (m, 1H), 2.65-2.73 (m, 1H), 2.73-2.84 (m, 3H), 3.18-3.24 (m, 1H), 3.24-3.32 (m, 2H), 3.38-3.46 (m, 1H), 3.69 (d, J=8.83 Hz, 1H), 3.92-3.99 (m, 1H), 7.86-7.91 (m, 1H), 7.93 (td, J=7.65, 1.42 Hz, 1H), 8.01 (d, J=7.60 Hz, 1H), 8.05 (d, J=7.62 Hz, 1H), 12.65 (br. s., 1H)
optical purity 11.4% ee
<HPLC Analysis Conditions>
column: CHIRALPAK IC (manufactured by Daicel Corporation)
column temperature: constant temperature near 15° C.
mobile phase: Solution A) 0.02 mol/L KH$_2$PO$_4$ buffer (pH 3.0):acetonitrile=70:30
Solution B) 0.02 mol/L KH$_2$PO$_4$ buffer (pH 3.0):acetonitrile=50:50
Gradient Program

TABLE 16

| time (min) | Solution A (%) | Solution B (%) |
|---|---|---|
| 0 | 100 | 0 |
| 3 | 80 | 40 |
| 16 | 80 | 40 |
| 22 | 20 | 80 |
| 32 | 20 | 80 |
| 32.1 | 100 | 0 |
| 40 | 100 | 0 | flow: 0.5 mL/min
retention time: (3R,5S) form 19.1 min, (3S,5R) form 20.4 min

Example 18

(1R,3S)-3-(diethylcarbamoyl)cyclopentanecarboxylic acid (acid anhydride: 3-oxabicyclo[3.2.1]octane-2,4-dione; amine:diethylamine)
$^1$H NMR (500 MHz, DMSO-$d_6$) δ ppm 1.00 (t, J=7.09 Hz, 3H), 1.11 (t, J=7.09 Hz, 3H), 1.68-1.75 (m, 1H), 1.75-1.89 (m, 4H), 2.03 (dt, J=12.53, 7.61 Hz, 1H), 2.64-2.78 (m, 1H), 2.92-3.00 (m, 1H), 3.26 (q, J=7.25 Hz, 2H), 3.33 (q, J=7.25 Hz, 2H), 12.05 (br. s., 1H)
optical purity 10.7% ee
<HPLC Analysis Conditions>
column: CHIRALPAK IF (manufactured by Daicel Corporation)
column temperature: constant temperature near 15° C.
mobile phase: Solution A) 0.02 mol/L KH$_2$PO$_4$ buffer (pH 3.0):acetonitrile=70:30
Solution B) 0.02 mol/L KH$_2$PO$_4$ buffer (pH 3.0):acetonitrile=50:50
Gradient Program

TABLE 17

| time (min) | Solution A (%) | Solution B (%) |
|---|---|---|
| 0 | 100 | 0 |
| 16 | 0 | 100 |
| 35 | 0 | 100 |
| 35.1 | 100 | 0 |
| 41 | 100 | 0 | flow: 0.5 mL/min
retention time: (1R,3S) form 13.1 min, (1S,3R) form 14.2 min

Example 19

(1R,3S)-3-(morpholin-4-ylcarbonyl)cyclohexanecarboxylic acid (acid anhydride: 3-oxabicyclo[3.3.1]nonane-2,4-dione; amine: morpholine)
$^1$H NMR (500 MHz, DMSO-$d_6$) δ ppm 1.17-1.29 (m, 2H), 1.31-1.44 (m, 2H), 1.58-1.67 (m, 1H), 1.73-1.78 (m, 1H), 1.78-1.85 (m, 1H), 1.85-1.90 (m, 1H), 2.30 (tt, J=12.37, 3.55 Hz, 1H), 2.65 (tt, J=11.78, 3.19 Hz, 1H), 3.43 (br. s., 2H), 3.46-3.58 (m, 6H), 12.05 (s, 1H)
optical purity 88.3% ee
<HPLC Analysis Conditions>
column: CHIRALPAK IF (manufactured by Daicel Corporation)
column temperature: constant temperature near 15° C.
mobile phase: Solution A) 0.02 mol/L KH$_2$PO$_4$ buffer (pH 3.0):acetonitrile=70:30
Solution B) 0.02 mol/L KH$_2$PO$_4$ buffer (pH 3.0):acetonitrile=50:50
Gradient Program

TABLE 18

| time (min) | Solution A (%) | Solution B (%) |
|---|---|---|
| 0 | 100 | 0 |
| 3 | 80 | 40 |
| 16 | 80 | 40 |
| 22 | 20 | 80 |
| 32 | 20 | 80 |
| 32.1 | 100 | 0 |
| 40 | 100 | 0 | flow: 0.5 mL/min
retention time: (1R,3S) form 9.3 min, (1S,3R) form 15.7 min

Example 20

(3S,5R)-5-(morpholin-4-ylcarbonyl)-1-(trifluoroacetyl)piperidine-3-carboxylic acid (acid anhydride: 7-(2,2,2-trifluoroacetyl)-3-oxa-7-azabicyclo[3.3.1]nonane-2,4-dione; amine: morpholine)

¹H NMR (500 MHz, DMSO-d₆) δ ppm 1.65 (dd, J=12.77, 5.20 Hz, 1H), 2.11 (d, J=12.61 Hz, 1H), 2.64-2.73 (m, 1H), 2.87-2.96 (m, 1H), 2.96-3.05 (m, 1H), 3.25-3.39 (m, 2H), 3.41-3.50 (m, 2H), 3.51-3.61 (m, 5H), 3.70-4.06 (m, 1H), 4.20-4.60 (m, 1H), 12.74 (br. s., 1H)

optical purity 26.0% ee

<HPLC Analysis Conditions> column: CHIRALPAK IF (manufactured by Daicel Corporation)

column temperature: constant temperature near 15° C.

mobile phase: Solution A) 0.02 mol/L $KH_2PO_4$ buffer (pH 3.0):acetonitrile=70:30

Solution B) 0.02 mol/L $KH_2PO_4$ buffer (pH 3.0):acetonitrile=50:50

Gradient Program

TABLE 19

| time (min) | Solution A (%) | Solution B (%) |
|---|---|---|
| 0 | 100 | 0 |
| 3 | 80 | 40 |
| 16 | 80 | 40 |
| 22 | 20 | 80 |
| 32 | 20 | 80 |
| 32.1 | 100 | 0 |
| 40 | 100 | 0 | flow: 0.5 mL/min retention time: (3S,5R) form 11.1 min, (3R,5S) form 18.7 min

Example 21

(3S,5R)-1-(tertiary-butoxycarbonyl)-5-(morpholin-4-ylcarbonyl)piperidine-3-carboxylic acid To a reaction vessel were added THF (1.0 mL), aluminum trichloride (0.10 g) and morpholine (0.068 mL), and the mixture was stirred. To another reaction vessel were added THF (1 mL), quinidine (0.25 g) and tertiary-butyl 2,4-dioxo-3-oxa-7-azabicyclo[3.3.1]nonane-7-carboxylate (0.20 g) at -10° C., and the mixture was stirred. The morpholine solution prepared at the beginning was added dropwise to the other reaction vessel, and the mixture was reacted. The reaction mixture was analyzed by HPLC, and the optical purity of the resulting title compound was determined.

optical purity 17.3% ee

<HPLC Analysis Conditions> column: CHIRALPAK AD-H (manufactured by Daicel Corporation)

column temperature: constant temperature near 25° C.

mobile phase: n-hexane:ethanol:trifluoroacetic acid=80:20:0.1 analysis time: 30 min flow: 1.0 mL/min retention time: (3S,5R) form 9.1 min, (3R,5S) form 11.1 min Enantioselectivity was confirmed in the same compound also when aluminum trichloride of Example 21 was changed to the following aluminum compound.

aluminum tribromide
optical purity 12.5% ee
ethylaluminum dichloride
optical purity 22.8% ee
trimethylaluminum
optical purity -84.8% ee Example 22

(3S,5R)-1-(tertiary-butoxycarbonyl)-5-(morpholin-4-ylcarbonyl)piperidine-3-carboxylic acid To a reaction vessel were added THF (1.0 mL), trimethylaluminum 1.4M toluene solution (0.56 mL) and morpholine (0.068 mL), and the mixture was stirred. To another reaction vessel were added THF (1 mL), quinine (0.25 g) and tertiary-butyl 2,4-dioxo-3-oxa-7-azabicyclo[3.3.1]nonane-7-carboxylate (0.20 g) at -10° C., and the mixture was stirred. A morpholine solution prepared in advance was added dropwise to another reaction vessel, and the mixture was reacted. The reaction mixture was analyzed by HPLC, and the optical purity of the resulting title compound was determined.

optical purity 79.2% ee

<HPLC Analysis Conditions> column: CHIRALPAK AD-H (manufactured by Daicel Corporation)

column temperature: constant temperature near 25° C.

mobile phase: n-hexane:ethanol:trifluoroacetic acid=80:20:0.1 analysis time: 30 min flow: 1.0 mL/min retention time: (3S,5R) form 9.1 min, (3R,5S) form 11.1 min Enantioselectivity was confirmed in the same compound also when trimethylaluminum of Example 22 was changed to the following aluminum compound.

triethylaluminum
optical purity 73.5% ee
triisobutylaluminum
optical purity 69.3% ee
diethylaluminum chloride
optical purity -3.9% ee Example 23

(3S,5R)-1-(tertiary-butoxycarbonyl)-5-(morpholin-4-ylcarbonyl)piperidine-3-carboxylic acid To a reaction vessel were added chlorobenzene (4 mL) and hydroquinine (0.28 g), the mixture was stirred, and DIBAL 1.0M hexane solution (0.86 mL) was added dropwise. To this reaction mixture was added morpholine (0.068 mL), and the mixture was stirred for about 2 hr. The reaction mixture was cooled to -10° C., and tertiary-butyl 2,4-dioxo-3-oxa-7-azabicyclo[3.3.1]nonane-7-carboxylate (0.20 g) was added. The reaction mixture was analyzed by HPLC, and the optical purity of the resulting title compound was determined.

optical purity 41.0% ee

<HPLC Analysis Conditions> column: CHIRALPAK IE (manufactured by Daicel Corporation)

column temperature: constant temperature near 15° C.

mobile phase: 0.02 mol/L $KH_2PO_4$ buffer (pH 3.0): acetonitrile=70:30 analysis time: 38 min flow: 0.5 mL/min retention time: (3R,5S) form 18.6 min, (3S,5R) form 21.9 min Enantioselectivity was confirmed in the same compound also when hydroquinine of Example 23 was changed to the following cinchona alkaloid.
  hydroquinidine
optical purity −45.2% ee
  cinchonine
optical purity −9.5% ee
  cinchonidine
optical purity 7.8% ee
  quinidine
optical purity −42.5% ee

Example 24

(3S,5R)-1-(tertiary-butoxycarbonyl)-5-(morpholin-4-ylcarbonyl)piperidine-3-carboxylic acid To a reaction vessel were added chlorobenzene (4 mL) and quinine (0.28 g), the mixture was stirred, and DIBAL 1.0M hexane solution (0.86 mL) was added dropwise. To this reaction mixture were added morpholine (0.068 mL) and DBU (0.12 mL), and the mixture was stirred for about 2 hr. The reaction mixture was cooled to −10° C., and tertiary-butyl 2,4-dioxo-3-oxa-7-azabicyclo[3.3.1]nonane-7-carboxylate (0.20 g) was added. The reaction mixture was analyzed by HPLC, and the optical purity of the resulting title compound was determined.
optical purity 1.8% ee
<HPLC Analysis Conditions>
column: CHIRALPAK IE (manufactured by Daicel Corporation)
column temperature: constant temperature near 15° C.
mobile phase: 0.02 mol/L $KH_2PO_4$ buffer (pH 3.0): acetonitrile=70:30
analysis time: 38 min
flow: 0.5 mL/min
retention time: (3R,5S) form 18.6 min, (3S,5R) form 21.9 min Enantioselectivity was confirmed in the same compound also when DBU of Example 24 was changed to the following base.
  sodium hydride
optical purity 39.0% ee
  sodium hydrogen carbonate
optical purity 40.7% ee
  sodium carbonate
optical purity 39.4% ee
  potassium carbonate
optical purity 24.6% ee
  cesium carbonate
optical purity 3.6% ee
  tertiary-butoxy sodium
optical purity 40.7% ee
  tertiary-butoxy potassium
optical purity 41.0% ee
  hexamethyldisilazane lithium
optical purity 33.3% ee
  isopropylmagnesium chloride
optical purity 4.2% ee
  normal butyllithium
optical purity 29.4% ee In the same manner as in Example 1 and using the corresponding acid anhydride and amine, the compounds of the following Examples 25-28 were synthesized.

Example 25

(1R,3S)-3-(piperidine-1-carbonyl)cyclohexanecarboxylic acid (acid anhydride: 3-oxabicyclo[3.3.1]nonane-2,4-dione; amine:piperidine)
$^1$H NMR (500 MHz, DMSO-$d_6$) δ ppm 1.14-1.29 (m, 2H), 1.31-1.44 (m, 4H), 1.49 (br. s., 2H), 1.54-1.63 (m, 3H), 1.72-1.82 (m, 2H), 1.87 (d, J=12.61 Hz, 1H), 2.31 (tt, J=12.41, 3.35 Hz, 1H), 2.65 (tt, J=11.78, 3.19 Hz, 1H), 3.38-3.46 (m, 4H), 12.06 (s, 1H)
optical purity 81.5% ee
<HPLC Analysis Conditions>
column: CHIRALPAK IF (manufactured by Daicel Corporation)
column temperature: constant temperature near 15° C.
mobile phase: Solution A) 0.02 mol/L$KH_2PO_4$ buffer (pH 3.0):acetonitrile=70:30
  Solution B) 0.02 mol/L$KH_2PO_4$ buffer (pH 3.0):acetonitrile=50:50
Gradient Program

TABLE 20

| time (min) | Solution A (%) | Solution B (%) |
|---|---|---|
| 0 | 100 | 0 |
| 3 | 80 | 40 |
| 16 | 80 | 40 |
| 22 | 20 | 80 |
| 32 | 20 | 80 |
| 32.1 | 100 | 0 |
| 40 | 100 | 0 | flow: 0.5 mL/min
retention time: (1R,3S) form 14.8 min, (1S,3R) form 19.0 min

Example 26

(1R,2S)-2-(piperidine-1-carbonyl)cyclohexanecarboxylic acid (acid anhydride: cis-1,2-cyclohexanedicarboxylic acid anhydride; amine: piperidine)
$^1$H NMR (500 MHz, DMSO-$d_6$) δ ppm 1.18-1.32 (m, 2H), 1.34-1.43 (m, 3H), 1.45-1.55 (m, 3H), 1.58 (d, J=4.41 Hz, 2H), 1.66-1.76 (m, 2H), 1.76-1.83 (m, 1H), 2.08-2.18 (m, 1H), 2.38 (dt, J=9.77, 4.57 Hz, 1H), 3.21 (q, J=4.62 Hz, 1H), 3.30 (br. s., 1H), 3.35-3.40 (m, 1H), 3.40-3.51 (m, 2H), 11.84 (br. s., 1H)
optical purity 8.4% ee
<HPLC Analysis Conditions>
column: CHIRALPAK IF (manufactured by Daicel Corporation)
column temperature: constant temperature near 15° C.
mobile phase: Solution A) 0.02 mol/L$KH_2PO_4$ buffer (pH 3.0):acetonitrile=70:30

Solution B) 0.02 mol/LKH$_2$PO$_4$ buffer (pH 3.0):acetonitrile=50:50
Gradient Program

TABLE 21

| time (min) | Solution A (%) | Solution B (%) |
|---|---|---|
| 0 | 100 | 0 |
| 3 | 80 | 40 |
| 16 | 80 | 40 |
| 22 | 20 | 80 |
| 32 | 20 | 80 |
| 32.1 | 100 | 0 |
| 40 | 100 | 0 | flow: 0.5 mL/min
retention time: (1S,2R) form 23.2 min, (1R,2S) form 24.4 min

Example 27

(1R,3S)-3-(piperidine-1-carbonyl)cyclopentanecarboxylic acid (acid anhydride: 3-oxabicyclo[3.2.1]octane-2,4-dione; amine: piperidine)
$^1$H NMR (500 MHz, DMSO-d$_6$) δ ppm 1.37-1.44 (m, 2H), 1.44-1.51 (m, 2H), 1.54-1.62 (m, 2H), 1.69-1.79 (m, 3H), 1.79-1.89 (m, 2H), 2.02 (dt, J=12.61, 7.72 Hz, 1H), 2.64-2.75 (m, 1H), 2.96-3.08 (m, 1H), 3.38-3.48 (m, 4H), 12.07 (br. s., 1H)
optical purity 37.0% ee
<HPLC Analysis Conditions>
column: CHIRALPAK IF (manufactured by Daicel Corporation)
column temperature: constant temperature near 15° C.
mobile phase: Solution A) 0.02 mol/LKH$_2$PO$_4$ buffer (pH 3.0):acetonitrile=70:30
Solution B) 0.02 mol/LKH$_2$PO$_4$ buffer (pH 3.0):acetonitrile=50:50
Gradient Program

TABLE 22

| time (min) | Solution A (%) | Solution B (%) |
|---|---|---|
| 0 | 100 | 0 |
| 3 | 80 | 40 |
| 16 | 80 | 40 |
| 22 | 20 | 80 |
| 32 | 20 | 80 |
| 32.1 | 100 | 0 |
| 40 | 100 | 0 | flow: 0.5 mL/min
retention time: (1R,3S) form 15.4 min, (1S,3R) form 17.0 min

Example 28

(3S,5R)-5-(piperidine-1-carbonyl)-1-tritylpiperidine-3-carboxylic acid (acid anhydride: 7-trityl-3-oxa-7-azabicyclo[3.3.1]nonane-2,4-dione; amine: piperidine)
$^1$H NMR (500 MHz, DMSO-d$_6$) δ ppm 1.12-1.22 (m, 3H), 1.23-1.32 (m, 2H), 1.34-1.42 (m, 1H), 1.47 (dt, J=9.62, 2.92 Hz, 1H), 1.50-1.60 (m, 2H), 1.88-1.95 (m, 1H), 2.88-2.96 (m, 1H), 2.99 (d, J=11.03 Hz, 1H), 3.18 (ddd, J=12.45, 8.67, 3.47 Hz, 1H), 3.22-3.31 (m, 2H), 3.42-3.58 (m, 3H), 7.10-7.54 (m, 15H), 12.29 (br. s., 1H)
optical purity 16.4% ee
<HPLC Analysis Conditions>
column: CHIRALPAK IB (manufactured by Daicel Corporation)
column temperature: constant temperature near 15° C.
mobile phase: Solution A) 0.02 mol/LKH$_2$PO$_4$ buffer (pH 3.0):acetonitrile=70:30
Solution B) 0.02 mol/LKH$_2$PO$_4$ buffer (pH 3.0):acetonitrile=50:50
Gradient Program

TABLE 23

| time (min) | Solution A (%) | Solution B (%) |
|---|---|---|
| 0 | 100 | 0 |
| 5 | 0 | 100 |
| 45 | 0 | 100 |
| 45.1 | 100 | 0 |
| 60 | 100 | 0 | flow: 0.5 mL/min
retention time: (3S,5R) form 46.6 min, (3R,5S) form 51.3 min

In the same manner as in Example 11 and using the corresponding acid anhydride and amine, the compounds of the following Examples 29-30 were synthesized.

Example 29

(1R,2S)-2-(morpholin-4-ylcarbonyl)cyclohexanecarboxylic acid (acid anhydride: cis-1,2-cyclohexanedicarboxylic acid anhydride; amine: morpholine)
$^1$H NMR (500 MHz, DMSO-d$_6$), δ ppm 1.29-1.38 (m, 2H), 1.42-1.50 (m, 2H), 1.53 (d, J=11.35 Hz, 2H), 1.74-1.90 (m, 2H), 2.53-2.58 (m, 2H), 2.90-2.94 (m, 4H), 3.63-3.67 (m, 4H), 10.83 (s, 1H)
optical purity 4.4% ee
<HPLC Analysis Conditions>
column: CHIRALPAK IB (manufactured by Daicel Corporation)
column temperature: constant temperature near 15° C.
mobile phase: Solution A) 0.02 mol/LKH$_2$PO$_4$ buffer (pH 3.0): MeOH=70:30
Solution B) 0.02 mol/LKH$_2$PO$_4$ buffer (pH 3.0): MeOH=50:50
Gradient Program

TABLE 24

| time (min) | Solution A (%) | Solution B (%) |
|---|---|---|
| 0 | 100 | 0 |
| 3 | 80 | 40 |
| 16 | 80 | 40 |
| 22 | 20 | 80 |
| 32 | 20 | 80 |
| 32.1 | 100 | 0 |
| 50 | 100 | 0 | flow: 0.5 mL/min
retention time: (1S,2R) form 34.8 min, (1R,2S) form 37.7 min

Example 30

(1R,3S)-3-(morpholin-4-ylcarbonyl)cyclopentanecarboxylic acid (acid anhydride: 3-oxabicyclo[3.2.1]octane-2,4-dione; amine: morpholine)

$^1$H NMR (500 MHz, DMSO-$d_6$) δ ppm 1.72-1.91 (m, 5H), 2.04 (dt, J=12.69, 7.84 Hz, 1H), 2.65-2.74 (m, 1H), 2.99-3.07 (m, 1H), 3.42-3.51 (m, 4H), 3.51-3.58 (m, 4H), 11.96-12.17 (m, 1H)

optical purity 52.3% ee

<HPLC Analysis Conditions>
column: CHIRALPAK IF (manufactured by Daicel Corporation)
column temperature: constant temperature near 15° C.
mobile phase: Solution A) 0.02 mol/LKH$_2$PO$_4$ buffer (pH 3.0):acetonitrile=70:30
Solution B) 0.02 mol/LKH$_2$PO$_4$ buffer (pH 3.0):acetonitrile=50:50
Gradient Program

TABLE 25

| time (min) | Solution A (%) | Solution B (%) |
|---|---|---|
| 0 | 100 | 0 |
| 3 | 80 | 40 |
| 16 | 80 | 40 |
| 22 | 20 | 80 |
| 32 | 20 | 80 |
| 32.1 | 100 | 0 |
| 40 | 100 | 0 | flow: 0.5 mL/min
retention time: (1R,3S) form 8.8 min, (1S,3R) form 10.0 min

INDUSTRIAL APPLICABILITY

The production method of the present invention is an amidation method of an acid anhydride, which is convenient and shows high enantioselectivity or diastereoselectivity. The method is useful as a production method of a synthetic intermediate for a heterocyclic compound having a renin inhibitory activity and useful as a prophylactic or therapeutic drug for diabetic nephropathy, hypertension and the like.

This application is based on patent application No. 2014-080984 filed in Japan, the contents of which are encompassed in full herein.

The invention claimed is:

1. A production method of a compound represented by the formula (III-1a), the formula (III-1b), the formula (III-1c) and/or the formula (III-1d);

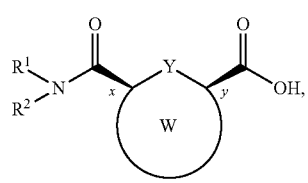
(III-1a)

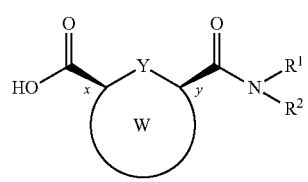
(III-1b)

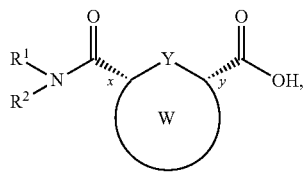
(III-1c)

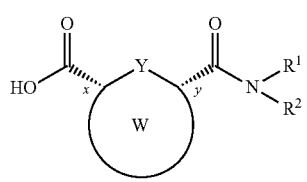
(III-1d)

wherein R$^1$ and R$^2$ are each independently a hydrogen atom or a substituent, or R$^1$ and R$^2$ are optionally bonded to each other to form an optionally substituted ring;
ring W is an optionally substituted ring;
Y is a carbon atom or a bond; and
x and y are each a bond, or a salt thereof, comprising reacting a compound represented by the formula (Ia) or (Ib):

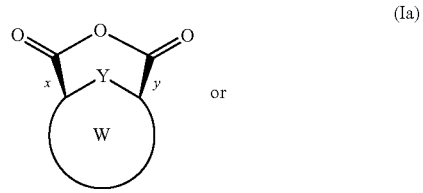
(Ia)

or

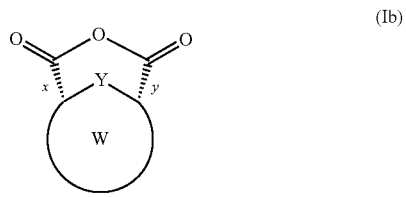
(Ib)

wherein each symbol is as defined above, or a salt thereof, with a compound represented by the formula (II):

(II)

wherein each symbol is as defined above, or a salt thereof, in the presence of an aluminum compound and a chiral amine compound.

2. The production method according to claim 1, wherein the ring W is a ring represented by the formula:

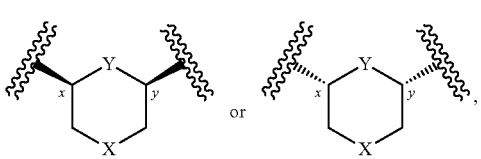

-continued

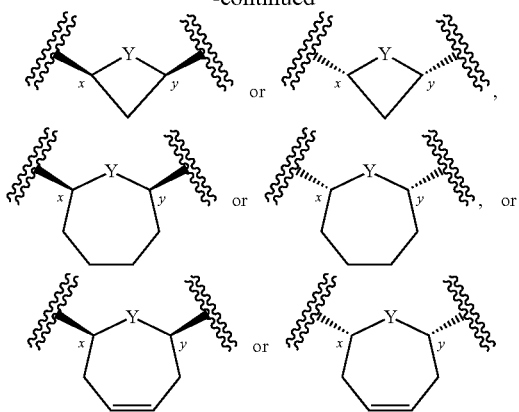

wherein
X is an optionally substituted carbon atom or an optionally substituted nitrogen atom,
and other symbols are as defined above.

3. The production method according to claim 1, wherein the ring W is a ring represented by the formula:

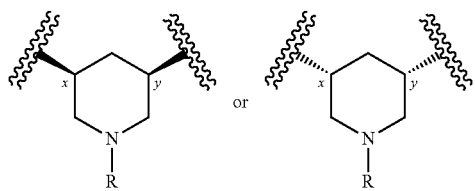

wherein
R is an amino-protecting group,
and other symbols are as defined above.

4. The production method according to claim 3, wherein R is a tertiary-butoxycarbonyl group.

5. The production method according to claim 1, wherein the chiral amine compound is cinchona alkaloid.

6. The production method according to claim 5, wherein cinchona alkaloid is quinine.

7. The production method according to claim 1, wherein $R^1$ and $R^2$ in the compound represented by the formula (II) are each independently a hydrogen atom, an optionally substituted $C_{1-6}$ alkyl group or an optionally substituted $C_{1-6}$ alkoxy group; or $R^1$ and $R^2$ are bonded to each other to form a non-aromatic heterocycle.

8. The production method according to claim 1, wherein the compound represented by the formula (II) is morpholine or a salt thereof.

9. The production method according to claim 1, wherein the aluminum compound is dialkylaluminum hydride, dihalogenated aluminum hydride, monohalogenated monoalkylaluminum hydride, trialkylaluminum, trihalogenated aluminum, monohalogenated dialkylaluminum or dihalogenated monoalkylaluminum.

10. The production method according to claim 1, wherein the aluminum compound is diisobutylaluminum hydride.

11. A production method of (3S,5R)-1-(tertiary-butoxycarbonyl)-5-(morpholin-4-ylcarbonyl)piperidine-3-carboxylic acid or a salt thereof, comprising reacting tertiary-butyl 2,4-dioxo-3-oxa-7-azabicyclo[3.3.1]nonane-7-carboxylate or a salt thereof with morpholine in the presence of an aluminum compound and a chiral amine compound.

12. A production method of 1-(4-methoxybutyl)-N-(2-methylpropyl)-N-[(3S,5R)-5-(morpholin-4-ylcarbonyl)piperidin-3-yl]-1H-benzimidazole-2-carboxamide or a salt thereof, comprising a step of producing (3S,5R)-1-(tertiary-butoxycarbonyl)-5-(morpholin-4-ylcarbonyl)piperidine-3-carboxylic acid or a salt thereof by reacting tertiary-butyl 2,4-dioxo-3-oxa-7-azabicyclo[3.3.1]nonane-7-carboxylate or a salt thereof with morpholine in the presence of an aluminum compound and a chiral amine compound.

* * * * *